(12) United States Patent
Dagan et al.

(10) Patent No.: US 10,828,181 B2
(45) Date of Patent: Nov. 10, 2020

(54) ANNULAR ANTENNA

(71) Applicant: Enopace Biomedical Ltd., Caesarea Industrial Park (IL)

(72) Inventors: Amir Dagan, Kibbutz Megiddo (IL); Nitai Hanani, Haifa (IL); Gal Ariav, Givat Ada (IL); Igor Gindin, Nesher (IL); Yossi Gross, Moshav Mazor (IL)

(73) Assignee: Enopace Biomedical Ltd., Caesarea Industrial Park (IL)

( * ) Notice: Subject to any disclaimer, the term of this patent is extended or adjusted under 35 U.S.C. 154(b) by 0 days.

(21) Appl. No.: 15/354,313

(22) Filed: Nov. 17, 2016

(65) Prior Publication Data

US 2017/0065824 A1 Mar. 9, 2017

Related U.S. Application Data

(63) Continuation of application No. 13/741,154, filed as application No. PCT/IL2012/000336 on Sep. 9, 2012, now Pat. No. 9,526,637.

(Continued)

(51) Int. Cl.
*A61F 2/82* (2013.01)
*A61F 2/915* (2013.01)
(Continued)

(52) U.S. Cl.
CPC ............ *A61F 2/82* (2013.01); *A61B 5/0215* (2013.01); *A61B 5/04* (2013.01); *A61B 5/0402* (2013.01); *A61B 5/0816* (2013.01); *A61F 2/848* (2013.01); *A61F 2/915* (2013.01); *A61N 1/05* (2013.01); *A61N 1/0558* (2013.01);
(Continued)

(58) Field of Classification Search
CPC ........... A61F 2/07–2202/077; A61F 2/82–948; A61F 2/24–2475; A61F 225/0001–0002
See application file for complete search history.

(56) References Cited

U.S. PATENT DOCUMENTS 3,650,277 A 3/1972 Sjostrand et al.
3,661,148 A 5/1972 Kolin
(Continued)

FOREIGN PATENT DOCUMENTS

EP 0109935 A1 5/1984
EP 0791341 A1 8/1997
(Continued)

OTHER PUBLICATIONS

"Stent", Free Online Medical Dictionary, pp. 1-3, accessed Jul. 17, 2013. (Year: 2013).*
(Continued)

*Primary Examiner* — Rebecca S Preston
(74) *Attorney, Agent, or Firm* — Locke Lord LLP

(57) ABSTRACT

Apparatus and methods are described for use with a blood vessel of a subject. An annular antenna is placed inside the blood vessel such that radial expansion of the antenna is limited by a circumference of the blood vessel. A transmitter generates an inductive current in the antenna, by transmitting RF energy toward the antenna. A control unit measures the inductive current in the antenna, and, in response thereto, determines a physiological parameter of the subject. Other applications are also described.

16 Claims, 16 Drawing Sheets

Related U.S. Application Data

(60) Provisional application No. 61/532,660, filed on Sep. 9, 2011.

(51) Int. Cl.

| | | |
|---|---|---|
| *A61N 1/375* | (2006.01) | |
| *A61N 1/05* | (2006.01) | |
| *A61N 1/36* | (2006.01) | |
| *A61F 2/848* | (2013.01) | |
| *A61B 5/04* | (2006.01) | |
| *A61B 5/0215* | (2006.01) | |
| *A61B 5/0402* | (2006.01) | |
| *A61B 5/08* | (2006.01) | |
| *A61N 1/40* | (2006.01) | |

(52) U.S. Cl.
CPC ....... *A61N 1/36053* (2013.01); *A61N 1/3756* (2013.01); *A61N 1/40* (2013.01); *A61F 2002/825* (2013.01); *A61F 2002/8483* (2013.01); *A61F 2002/91541* (2013.01); *A61F 2002/91558* (2013.01); *A61F 2002/91575* (2013.01); *A61F 2210/0014* (2013.01); *A61F 2220/005* (2013.01); *A61F 2220/0016* (2013.01); *A61F 2220/0075* (2013.01); *A61F 2230/0054* (2013.01); *A61F 2250/0001* (2013.01); *A61F 2250/0002* (2013.01); *A61F 2250/008* (2013.01); *A61F 2250/0018* (2013.01); *A61F 2250/0037* (2013.01); *A61F 2250/0096* (2013.01); *A61N 1/056* (2013.01); *A61N 1/057* (2013.01); *A61N 1/0514* (2013.01); *A61N 2001/0585* (2013.01)

(56) References Cited

U.S. PATENT DOCUMENTS

| | | |
|---|---|---|
| 4,154,227 A | 5/1979 | Krause et al. |
| 4,201,219 A | 5/1980 | Bozal Gonzalez et al. |
| 4,474,630 A | 10/1984 | Planck et al. |
| 4,692,148 A | 9/1987 | Kantrowitz et al. |
| 4,791,931 A | 12/1988 | Slate |
| 4,809,681 A | 3/1989 | Kantrowitz et al. |
| 4,821,723 A | 4/1989 | Baker, Jr. et al. |
| 4,848,352 A | 7/1989 | Pohndorf et al. |
| 4,938,766 A | 7/1990 | Jarvik |
| 5,192,271 A | 3/1993 | Kalb et al. |
| 5,199,428 A | 4/1993 | Obel et al. |
| 5,224,491 A | 7/1993 | Mehra |
| 5,265,011 A | 11/1993 | O'Rourke |
| 5,265,601 A | 11/1993 | Mehra |
| 5,306,292 A | 4/1994 | Lindegren |
| 5,324,323 A | 6/1994 | Bui |
| 5,330,507 A | 7/1994 | Schwartz |
| 5,372,573 A | 12/1994 | Habib |
| 5,411,031 A | 5/1995 | Yomtov |
| 5,423,871 A | 6/1995 | Hoegnelid et al. |
| 5,458,626 A | 10/1995 | Krause |
| 5,487,760 A | 1/1996 | Villafana |
| 5,540,730 A | 7/1996 | Terry, Jr. et al. |
| 5,571,150 A | 11/1996 | Wernicke et al. |
| 5,612,314 A | 3/1997 | Stamler et al. |
| 5,645,839 A | 7/1997 | Chobanian et al. |
| 5,649,966 A | 7/1997 | Noren et al. |
| 5,651,378 A | 7/1997 | Matheny et al. |
| 5,669,924 A | 9/1997 | Shaknovich |
| 5,690,681 A | 11/1997 | Geddes et al. |
| 5,707,400 A | 1/1998 | Terry, Jr. et al. |
| 5,735,887 A | 4/1998 | Barreras, Sr. et al. |
| 5,762,599 A | 6/1998 | Sohn |
| 5,782,774 A | 7/1998 | Shmulewitz |
| 5,800,464 A | 9/1998 | Kieval |
| 5,800,502 A | 9/1998 | Boutos |
| 5,814,089 A | 9/1998 | Stokes et al. |
| 5,873,865 A | 2/1999 | Horzewski et al. |
| 5,900,433 A | 5/1999 | Igo et al. |
| 5,902,712 A | 5/1999 | Burns et al. |
| 5,904,711 A | 5/1999 | Flom et al. |
| 5,904,712 A | 5/1999 | Axelgaard |
| 5,906,641 A | 5/1999 | Thompson et al. |
| 5,913,876 A | 6/1999 | Taylor et al. |
| 5,935,077 A | 8/1999 | Ogle |
| 5,948,006 A | 9/1999 | Mann |
| 5,994,444 A | 11/1999 | Trescony et al. |
| 6,014,589 A | 1/2000 | Farley et al. |
| 6,023,640 A | 2/2000 | Ross |
| 6,029,091 A | 2/2000 | de la Rama et al. |
| 6,038,485 A | 3/2000 | Axelgaard |
| 6,053,873 A | 4/2000 | Govari et al. |
| 6,058,331 A | 5/2000 | King |
| 6,073,048 A | 6/2000 | Kieval et al. |
| 6,086,527 A | 7/2000 | Talpade |
| 6,104,956 A | 8/2000 | Naritoku et al. |
| 6,106,477 A | 8/2000 | Miesel et al. |
| 6,120,520 A | 9/2000 | Saadat et al. |
| 6,141,587 A | 10/2000 | Mower |
| 6,178,349 B1 | 1/2001 | Kieval |
| 6,200,259 B1 | 3/2001 | March |
| 6,201,991 B1 | 3/2001 | Chekanov |
| 6,231,516 B1 | 5/2001 | Keilman et al. |
| 6,245,103 B1 | 6/2001 | Stinson |
| 6,246,911 B1 | 6/2001 | Seligman |
| 6,270,524 B1 | 8/2001 | Kim |
| 6,273,910 B1 | 8/2001 | Limon |
| 6,277,078 B1 | 8/2001 | Porat et al. |
| 6,292,695 B1 | 9/2001 | Webster, Jr. et al. |
| 6,317,631 B1 | 11/2001 | Ben-Haim et al. |
| 6,339,725 B1 | 1/2002 | Naritoku et al. |
| 6,347,247 B1 | 2/2002 | Dev et al. |
| 6,411,845 B1 | 6/2002 | Mower |
| 6,418,348 B1 | 7/2002 | Witte |
| 6,423,084 B1 | 7/2002 | St. Germain |
| 6,440,059 B1 | 8/2002 | Haas et al. |
| 6,445,953 B1 | 9/2002 | Bulkes et al. |
| 6,463,323 B1 | 10/2002 | Conrad-Vlasak et al. |
| 6,473,644 B1 | 10/2002 | Terry, Jr. et al. |
| 6,480,747 B2 | 11/2002 | Schmidt |
| 6,485,524 B2 | 11/2002 | Strecker |
| 6,496,732 B1 | 12/2002 | Wallace |
| 6,522,926 B1 | 2/2003 | Kieval et al. |
| 6,532,388 B1 | 3/2003 | Hill et al. |
| 6,582,461 B1 | 6/2003 | Burmeister et al. |
| 6,611,715 B1 | 8/2003 | Boveja |
| 6,615,085 B1 | 9/2003 | Boveja |
| 6,616,613 B1 | 9/2003 | Goodman |
| 6,616,624 B1 | 9/2003 | Kieval |
| 6,622,041 B2 | 9/2003 | Terry, Jr. et al. |
| 6,626,935 B1 | 9/2003 | Ainsworth et al. |
| 6,631,296 B1 | 10/2003 | Parramon et al. |
| 6,632,991 B2 | 10/2003 | Chen |
| 6,647,287 B1 | 11/2003 | Peel, III et al. |
| 6,656,960 B2 | 12/2003 | Puskas |
| 6,668,191 B1 | 12/2003 | Boveja |
| 6,682,480 B1 | 1/2004 | Habib et al. |
| 6,721,603 B2 | 4/2004 | Zabara et al. |
| 6,735,474 B1 | 5/2004 | Loeb et al. |
| 6,810,286 B2 | 10/2004 | Donovan et al. |
| 6,824,561 B2 | 11/2004 | Soykan et al. |
| 6,845,267 B2 | 1/2005 | Harrison et al. |
| 6,850,801 B2 | 2/2005 | Kieval et al. |
| 6,865,416 B2 | 3/2005 | Dev et al. |
| 6,871,092 B2 | 3/2005 | Piccone |
| 6,885,895 B1 | 4/2005 | Whitehurst et al. |
| 6,934,583 B2 | 8/2005 | Weinberg et al. |
| 6,939,345 B2 | 9/2005 | Kenknight et al. |
| 6,947,792 B2 | 9/2005 | Ben-Haim et al. |
| 6,985,774 B2 | 1/2006 | Kieval et al. |
| 7,044,981 B2 | 5/2006 | Liu et al. |
| 7,062,318 B2 | 6/2006 | Ben-Haim et al. |
| 7,076,307 B2 | 7/2006 | Boveja et al. |
| 7,079,901 B1 | 7/2006 | Loftin et al. |
| 7,082,336 B2 | 7/2006 | Ransbury et al. |
| 7,090,648 B2 | 8/2006 | Sackner et al. |

(56) References Cited

U.S. PATENT DOCUMENTS

| | | |
|---|---|---|
| 7,123,961 B1 | 10/2006 | Kroll et al. |
| 7,149,574 B2 | 12/2006 | Yun et al. |
| 7,158,832 B2 | 1/2007 | Kieval et al. |
| 7,167,751 B1 | 1/2007 | Whitehurst et al. |
| 7,191,007 B2 | 3/2007 | Desai et al. |
| 7,191,012 B2 | 3/2007 | Boveja et al. |
| 7,201,719 B2 | 4/2007 | Feliss et al. |
| 7,206,637 B2 | 4/2007 | Salo |
| 7,225,019 B2 | 5/2007 | Jahns et al. |
| 7,228,167 B2 | 6/2007 | Kara et al. |
| 7,229,403 B2 | 6/2007 | Schock et al. |
| 7,263,405 B2 | 8/2007 | Boveja et al. |
| 7,269,457 B2 | 9/2007 | Shafer et al. |
| 7,277,761 B2 | 10/2007 | Shelchuk |
| 7,291,113 B2 | 11/2007 | Satoh et al. |
| 7,292,886 B1 | 11/2007 | Kroll |
| 7,299,091 B2 | 11/2007 | Barrett et al. |
| 7,321,793 B2 | 1/2008 | Ben Ezra et al. |
| 7,363,076 B2 | 4/2008 | Yun et al. |
| 7,367,970 B2 | 5/2008 | Govari et al. |
| 7,389,149 B2 | 6/2008 | Rossing et al. |
| 7,395,119 B2 | 7/2008 | Hagen et al. |
| 7,444,183 B2 | 10/2008 | Knudson et al. |
| 7,452,334 B2 | 11/2008 | Gianchandani et al. |
| 7,471,986 B2 | 12/2008 | Hatlestad |
| 7,476,200 B2 | 1/2009 | Tal |
| 7,480,532 B2 | 1/2009 | Kieval et al. |
| 7,486,991 B2 | 2/2009 | Libbus et al. |
| 7,499,747 B2 | 3/2009 | Kieval et al. |
| 7,499,748 B2 | 3/2009 | Moffitt et al. |
| 7,502,650 B2 | 3/2009 | Kieval |
| 7,519,421 B2 | 4/2009 | Denker et al. |
| 7,532,932 B2 | 5/2009 | Denker et al. |
| 7,555,344 B2 | 6/2009 | Maschino et al. |
| 7,561,918 B2 | 7/2009 | Armstrong et al. |
| 7,570,999 B2 | 8/2009 | Libbus et al. |
| 7,613,511 B2 | 11/2009 | Wu et al. |
| 7,613,515 B2 | 11/2009 | Knudson et al. |
| 7,616,997 B2 | 11/2009 | Kieval et al. |
| 7,617,003 B2 | 11/2009 | Caparso et al. |
| 7,623,926 B2 | 11/2009 | Rossing et al. |
| 7,634,315 B2 | 12/2009 | Cholette |
| 7,706,875 B2 | 4/2010 | Buras et al. |
| 7,706,884 B2 | 4/2010 | Libbus |
| 7,706,886 B2 | 4/2010 | Morimoto et al. |
| 7,715,915 B1 | 5/2010 | Ryu et al. |
| 7,720,547 B2 | 5/2010 | Denker et al. |
| 7,725,194 B2 | 5/2010 | Klostermann et al. |
| 7,738,961 B2 | 6/2010 | Sharma |
| 7,747,302 B2 | 6/2010 | Milledge et al. |
| 7,765,000 B2 | 7/2010 | Zhang et al. |
| 7,765,008 B2 | 7/2010 | Ben-Haim et al. |
| 7,769,446 B2 | 8/2010 | Moffitt et al. |
| 7,780,719 B2 | 8/2010 | Killion et al. |
| 7,801,604 B2 | 9/2010 | Brockway et al. |
| 7,811,221 B2 | 10/2010 | Gross |
| 7,813,805 B1 | 10/2010 | Farazi |
| 7,813,812 B2 | 10/2010 | Kieval et al. |
| 7,826,899 B1 | 11/2010 | Ryu et al. |
| 7,840,282 B2 | 11/2010 | Williams et al. |
| 7,848,820 B2 | 12/2010 | Abrahamson |
| 7,856,273 B2 | 12/2010 | Maschino et al. |
| 7,860,566 B2 | 12/2010 | Mazgalev et al. |
| 7,869,870 B1 | 1/2011 | Farazi |
| 7,881,782 B2 | 2/2011 | Libbus et al. |
| 7,881,792 B1 | 2/2011 | Farazi |
| 7,894,902 B2 | 2/2011 | Rom |
| 7,899,554 B2 | 3/2011 | Williams et al. |
| 7,949,400 B2 | 5/2011 | Kieval et al. |
| 7,991,474 B2 | 8/2011 | Aldrich et al. |
| 8,046,085 B2 | 10/2011 | Knudson et al. |
| 8,065,019 B2 | 11/2011 | Marnfeldt et al. |
| 8,086,314 B1 | 12/2011 | Kieval |
| 8,095,218 B2 | 1/2012 | Gross et al. |
| 8,121,692 B2 | 2/2012 | Haefner et al. |
| 8,131,362 B2 | 3/2012 | Moffitt et al. |
| 8,150,508 B2 | 4/2012 | Craig |
| 8,160,701 B2 | 4/2012 | Zhao et al. |
| 8,175,705 B2 | 5/2012 | Libbus |
| 8,224,437 B2 | 7/2012 | Kieval et al. |
| 8,244,378 B2 | 8/2012 | Bly et al. |
| 8,249,705 B1 | 8/2012 | Kieval et al. |
| 8,290,595 B2 | 10/2012 | Kieval et al. |
| 8,386,038 B2 | 2/2013 | Bianchi et al. |
| 8,391,970 B2 | 3/2013 | Tracey et al. |
| 8,406,868 B2 | 3/2013 | Buschman et al. |
| 8,442,639 B2 | 5/2013 | Walker et al. |
| 8,449,472 B2 | 5/2013 | Ryu et al. |
| 8,457,743 B2 | 6/2013 | Gollasch et al. |
| 8,457,748 B2 | 6/2013 | Lange |
| 8,463,392 B2 | 6/2013 | Aghassian |
| 8,467,884 B2 | 6/2013 | Chen et al. |
| 8,478,414 B2 | 7/2013 | Kieval et al. |
| 8,498,704 B2 | 7/2013 | Shuros et al. |
| 8,504,161 B1 | 8/2013 | Kornet et al. |
| 8,509,919 B2 | 8/2013 | Yoo et al. |
| 8,521,293 B2 | 8/2013 | Anderson et al. |
| 8,538,535 B2 | 9/2013 | Gross et al. |
| 8,538,542 B2 | 9/2013 | Knudson et al. |
| 8,560,076 B2 | 10/2013 | Kieval et al. |
| 8,571,654 B2 | 10/2013 | Libbus et al. |
| 8,571,664 B2 | 10/2013 | Anderson et al. |
| 8,577,458 B1 | 11/2013 | Libbus et al. |
| 8,577,548 B2 | 11/2013 | Miller et al. |
| 8,600,505 B2 | 12/2013 | Libbus et al. |
| 8,600,511 B2 | 12/2013 | Yared et al. |
| 8,600,521 B2 | 12/2013 | Armstrong et al. |
| 8,606,359 B2 | 12/2013 | Rossing et al. |
| 8,612,014 B2 | 12/2013 | Rahman et al. |
| 8,620,422 B2 | 12/2013 | Kieval et al. |
| 8,620,450 B2 | 12/2013 | Tockman et al. |
| 8,626,290 B2 | 1/2014 | Dagan et al. |
| 8,626,299 B2 | 1/2014 | Gross et al. |
| 8,630,709 B2 | 1/2014 | Libbus et al. |
| 8,634,927 B2 | 1/2014 | Olson et al. |
| 8,634,928 B1 | 1/2014 | O'Driscoll et al. |
| 8,639,327 B2 | 1/2014 | Zhou et al. |
| 8,639,339 B2 | 1/2014 | Bange et al. |
| 8,644,928 B2 | 2/2014 | Takata |
| 8,660,666 B2 | 2/2014 | Craig |
| 8,663,103 B2 | 3/2014 | Causey, III et al. |
| 8,670,835 B2 | 3/2014 | Park et al. |
| 8,692,717 B2 | 4/2014 | Friedman |
| 8,700,145 B2 | 4/2014 | Kilgard et al. |
| 8,700,157 B2 | 4/2014 | Goetz et al. |
| 8,700,173 B2 | 4/2014 | Edlund |
| 8,706,223 B2 | 4/2014 | Zhou et al. |
| 8,712,531 B2 | 4/2014 | Kieval et al. |
| 8,729,129 B2 | 5/2014 | Tracey et al. |
| 8,731,663 B2 | 5/2014 | Bianchi et al. |
| 8,738,126 B2 | 5/2014 | Craig |
| 8,744,586 B2 | 6/2014 | Georgakopoulos et al. |
| 8,755,907 B2 | 6/2014 | Kieval et al. |
| 8,788,028 B2 | 7/2014 | Kumar et al. |
| 8,788,066 B2 | 7/2014 | Cates et al. |
| 8,805,513 B2 | 8/2014 | Libbus |
| 8,818,508 B2 | 8/2014 | Scheiner |
| 8,818,524 B2 | 8/2014 | Hincapie Ordonez et al. |
| 8,880,185 B2 | 11/2014 | Hastings et al. |
| 8,929,990 B2 | 1/2015 | Moffitt et al. |
| 2001/0044434 A1 | 11/2001 | Lee et al. |
| 2002/0016615 A1 | 2/2002 | Dev et al. |
| 2002/0026228 A1 | 2/2002 | Schauerte |
| 2002/0032468 A1 | 3/2002 | Hill et al. |
| 2002/0055764 A1 | 5/2002 | Malonek et al. |
| 2002/0077554 A1 | 6/2002 | Schwartz et al. |
| 2002/0089458 A1 | 7/2002 | Allen et al. |
| 2002/0103454 A1 | 8/2002 | Sackner et al. |
| 2002/0161377 A1 | 10/2002 | Rabkin |
| 2002/0169413 A1 | 11/2002 | Keren et al. |
| 2002/0198571 A1 | 12/2002 | Puskas |
| 2003/0036773 A1 | 2/2003 | Whitehurst et al. |
| 2003/0050683 A1 | 3/2003 | Boutos |
| 2003/0055465 A1 | 3/2003 | Ben-Haim et al. |

(56) References Cited

U.S. PATENT DOCUMENTS

| | | |
|---|---|---|
| 2003/0055466 A1 | 3/2003 | Ben-Haim et al. |
| 2003/0055467 A1 | 3/2003 | Ben-Haim et al. |
| 2003/0060858 A1 | 3/2003 | Kieval et al. |
| 2003/0109914 A1 | 6/2003 | Westlund et al. |
| 2003/0130715 A1 | 7/2003 | Boutos |
| 2003/0199806 A1 | 10/2003 | Kieval |
| 2003/0204206 A1 | 10/2003 | Padua et al. |
| 2004/0010303 A1 | 1/2004 | Bolea et al. |
| 2004/0015205 A1 | 1/2004 | Whitehurst et al. |
| 2004/0019364 A1 | 1/2004 | Kieval et al. |
| 2004/0039417 A1 | 2/2004 | Soykan et al. |
| 2004/0044393 A1 | 3/2004 | Yarden et al. |
| 2004/0054384 A1 | 3/2004 | Nachum |
| 2004/0064090 A1 | 4/2004 | Keren et al. |
| 2004/0082948 A1 | 4/2004 | Stewart et al. |
| 2004/0106954 A1 | 6/2004 | Whitehurst et al. |
| 2004/0106976 A1 | 6/2004 | Bailey et al. |
| 2004/0111006 A1 | 6/2004 | Alferness et al. |
| 2004/0133240 A1 | 7/2004 | Adams et al. |
| 2004/0162590 A1 | 8/2004 | Whitehurst et al. |
| 2004/0210261 A1 | 10/2004 | King et al. |
| 2004/0254616 A1 | 12/2004 | Rossing et al. |
| 2005/0027346 A1 | 2/2005 | Arkusz et al. |
| 2005/0033407 A1 | 2/2005 | Weber et al. |
| 2005/0049680 A1 | 3/2005 | Fischell et al. |
| 2005/0049686 A1 | 3/2005 | Gray et al. |
| 2005/0065592 A1 | 3/2005 | Holzer |
| 2005/0090867 A1 | 4/2005 | Lapanashvili et al. |
| 2005/0096710 A1 | 5/2005 | Kieval |
| 2005/0143785 A1 | 6/2005 | Libbus |
| 2005/0143789 A1 | 6/2005 | Whitehurst et al. |
| 2005/0149130 A1 | 7/2005 | Libbus |
| 2005/0149132 A1 | 7/2005 | Libbus |
| 2005/0149155 A1 | 7/2005 | Scheiner et al. |
| 2005/0149170 A1 | 7/2005 | Tassel et al. |
| 2005/0209652 A1 | 9/2005 | Whitehurst et al. |
| 2005/0233962 A1 | 10/2005 | Lue et al. |
| 2005/0240229 A1 | 10/2005 | Whitehurst et al. |
| 2005/0251212 A1 | 11/2005 | Kieval et al. |
| 2005/0283184 A1 | 12/2005 | Gilson et al. |
| 2005/0288651 A1 | 12/2005 | VanTassel et al. |
| 2006/0004417 A1 | 1/2006 | Rossing et al. |
| 2006/0004420 A1 | 1/2006 | Rossing et al. |
| 2006/0004430 A1 | 1/2006 | Rossing et al. |
| 2006/0074453 A1 | 4/2006 | Kieval et al. |
| 2006/0100668 A1 | 5/2006 | Ben-David et al. |
| 2006/0111626 A1 | 5/2006 | Rossing et al. |
| 2006/0149124 A1 | 7/2006 | Forsell |
| 2006/0149345 A1 | 7/2006 | Boggs et al. |
| 2006/0167540 A1 | 7/2006 | Masters et al. |
| 2006/0173507 A1 | 8/2006 | Mrva et al. |
| 2006/0217588 A1 | 9/2006 | Gross et al. |
| 2006/0217772 A1 | 9/2006 | Libbus et al. |
| 2006/0229677 A1 | 10/2006 | Moffitt et al. |
| 2006/0259085 A1 | 11/2006 | Zhang et al. |
| 2006/0265038 A1 | 11/2006 | Hagen et al. |
| 2006/0276844 A1 | 12/2006 | Alon et al. |
| 2006/0287705 A1* | 12/2006 | Weber .................. A61F 2/82 623/1.15 |
| 2006/0293712 A1 | 12/2006 | Kieval et al. |
| 2007/0021673 A1 | 1/2007 | Arbel et al. |
| 2007/0021786 A1 | 1/2007 | Parnis et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027496 A1 | 2/2007 | Parnis et al. |
| 2007/0038255 A1 | 2/2007 | Kieval et al. |
| 2007/0038259 A1 | 2/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0049989 A1 | 3/2007 | Rossing et al. |
| 2007/0060972 A1 | 3/2007 | Kieval et al. |
| 2007/0106340 A1 | 5/2007 | Bolea et al. |
| 2007/0142879 A1 | 6/2007 | Greenberg et al. |
| 2007/0150009 A1 | 6/2007 | Kveen et al. |
| 2007/0156179 A1 | 7/2007 | S.E. |
| 2007/0156198 A1 | 7/2007 | Rossing et al. |
| 2007/0156201 A1 | 7/2007 | Rossing |
| 2007/0167984 A1 | 7/2007 | Kieval et al. |
| 2007/0185540 A1 | 8/2007 | Ben-Haim et al. |
| 2007/0185542 A1 | 8/2007 | Bolea et al. |
| 2007/0185543 A1 | 8/2007 | Rossing et al. |
| 2007/0191904 A1 | 8/2007 | Libbus et al. |
| 2007/0196428 A1 | 8/2007 | Glauser et al. |
| 2007/0198064 A1 | 8/2007 | Lapanashvili et al. |
| 2007/0248676 A1 | 10/2007 | Stamler et al. |
| 2007/0248850 A1 | 10/2007 | Heller |
| 2007/0255379 A1 | 11/2007 | Williams et al. |
| 2007/0276270 A1 | 11/2007 | Tran |
| 2007/0276459 A1 | 11/2007 | Rossing et al. |
| 2007/0282385 A1 | 12/2007 | Rossing et al. |
| 2007/0288076 A1 | 12/2007 | Bulkes et al. |
| 2007/0293927 A1 | 12/2007 | Frank et al. |
| 2008/0004673 A1 | 1/2008 | Rossing et al. |
| 2008/0009916 A1 | 1/2008 | Rossing et al. |
| 2008/0009917 A1 | 1/2008 | Rossing et al. |
| 2008/0021336 A1 | 1/2008 | Dobak |
| 2008/0046016 A1 | 2/2008 | Ben-David et al. |
| 2008/0046054 A1 | 2/2008 | Hjelle et al. |
| 2008/0051767 A1 | 2/2008 | Rossing et al. |
| 2008/0051849 A1 | 2/2008 | Ben-Haim et al. |
| 2008/0058872 A1 | 3/2008 | Brockway et al. |
| 2008/0058889 A1 | 3/2008 | Ben-Haim et al. |
| 2008/0058891 A1 | 3/2008 | Ben-Haim et al. |
| 2008/0071363 A1 | 3/2008 | Tuval et al. |
| 2008/0077016 A1* | 3/2008 | Sparks .................. A61B 5/0031 600/459 |
| 2008/0082137 A1 | 4/2008 | Kieval et al. |
| 2008/0097540 A1 | 4/2008 | Bolea et al. |
| 2008/0119898 A1 | 5/2008 | Ben-David et al. |
| 2008/0119911 A1 | 5/2008 | Rosero |
| 2008/0132972 A1 | 6/2008 | Shuros et al. |
| 2008/0140167 A1 | 6/2008 | Hagen et al. |
| 2008/0147168 A1 | 6/2008 | Ransbury et al. |
| 2008/0154349 A1 | 6/2008 | Rossing et al. |
| 2008/0161865 A1 | 7/2008 | Hagen |
| 2008/0161887 A1 | 7/2008 | Hagen |
| 2008/0167690 A1 | 7/2008 | Cody et al. |
| 2008/0167693 A1 | 7/2008 | Kieval et al. |
| 2008/0167694 A1 | 7/2008 | Bolea et al. |
| 2008/0167696 A1 | 7/2008 | Cates et al. |
| 2008/0167699 A1 | 7/2008 | Kieval et al. |
| 2008/0171923 A1 | 7/2008 | Bolea et al. |
| 2008/0172101 A1 | 7/2008 | Bolea et al. |
| 2008/0172104 A1 | 7/2008 | Kieval et al. |
| 2008/0177364 A1 | 7/2008 | Bolea et al. |
| 2008/0183254 A1 | 7/2008 | Bly et al. |
| 2008/0195174 A1 | 8/2008 | Walker et al. |
| 2008/0215117 A1 | 9/2008 | Gross |
| 2009/0036975 A1 | 2/2009 | Ward et al. |
| 2009/0062874 A1 | 3/2009 | Tracey et al. |
| 2009/0112285 A1 | 4/2009 | Cahan et al. |
| 2009/0160716 A1 | 6/2009 | Rhodes et al. |
| 2009/0171425 A1 | 7/2009 | Dahlberg |
| 2009/0198097 A1 | 8/2009 | Gross |
| 2009/0198308 A1 | 8/2009 | Gross et al. |
| 2009/0204170 A1 | 8/2009 | Hastings et al. |
| 2009/0228078 A1 | 9/2009 | Zhang et al. |
| 2009/0248133 A1 | 10/2009 | Bloom et al. |
| 2009/0270951 A1 | 10/2009 | Kallmyer |
| 2010/0004650 A1 | 1/2010 | Ormsby et al. |
| 2010/0010556 A1 | 1/2010 | Zhao et al. |
| 2010/0042186 A1 | 2/2010 | Ben-David et al. |
| 2010/0052668 A1 | 3/2010 | Gleich et al. |
| 2010/0076247 A1 | 3/2010 | Zilbershlag et al. |
| 2010/0094373 A1 | 4/2010 | Sharma |
| 2010/0211131 A1 | 8/2010 | Williams et al. |
| 2010/0280568 A1* | 11/2010 | Bulkes .................. A61N 1/05 607/33 |

(56) References Cited

U.S. PATENT DOCUMENTS

| | | |
|---|---|---|
| 2010/0280593 A1 | 11/2010 | Richter |
| 2010/0305392 A1 | 12/2010 | Gross et al. |
| 2011/0106237 A1 | 5/2011 | Bonsignore et al. |
| 2011/0118773 A1 | 5/2011 | Gross et al. |
| 2011/0137370 A1 | 6/2011 | Gross et al. |
| 2011/0301760 A1 | 12/2011 | Shuster et al. |
| 2012/0003569 A1 | 1/2012 | Kawamura et al. |
| 2012/0035679 A1 | 2/2012 | Dagan et al. |
| 2012/0035711 A1 | 2/2012 | Gross et al. |
| 2012/0158081 A1 | 6/2012 | Gross et al. |
| 2012/0303112 A1 | 11/2012 | Armstrong et al. |
| 2013/0043736 A1 | 2/2013 | Zilbershlag |
| 2013/0123880 A1 | 5/2013 | Dagan et al. |
| 2013/0310629 A1 | 11/2013 | Lafontaine |
| 2013/0338748 A1 | 12/2013 | Dagan |
| 2014/0031607 A1 | 1/2014 | Zilbershlag et al. |
| 2014/0081154 A1* | 3/2014 | Toth ............... A61B 5/6862 600/479 |

FOREIGN PATENT DOCUMENTS

| | | |
|---|---|---|
| WO | WO-99026530 A1 | 6/1999 |
| WO | WO-00002501 A1 | 1/2000 |
| WO | WO-0226314 A1 | 4/2002 |
| WO | WO-03076008 A1 | 9/2003 |
| WO | WO-03082080 A2 | 10/2003 |
| WO | WO-03082403 A2 | 10/2003 |
| WO | WO-04014456 A2 | 2/2004 |
| WO | WO-04073484 A2 | 9/2004 |
| WO | WO-05/032414 A2 | 4/2005 |
| WO | WO-2005065771 A1 | 7/2005 |
| WO | WO-05084389 A2 | 9/2005 |
| WO | WO-05097256 A2 | 10/2005 |
| WO | WO-06012033 A2 | 2/2006 |
| WO | WO-06012050 A2 | 2/2006 |
| WO | WO-06032902 A1 | 3/2006 |
| WO | WO-06041664 A2 | 4/2006 |
| WO | WO-06064503 A2 | 6/2006 |
| WO | WO-06/089739 A1 | 8/2006 |
| WO | WO-2006/098928 A1 | 9/2006 |
| WO | WO-06094273 A2 | 9/2006 |
| WO | WO-06123346 A2 | 11/2006 |
| WO | WO-06125163 A2 | 11/2006 |
| WO | WO-07013065 A2 | 2/2007 |
| WO | WO-07047152 A2 | 4/2007 |
| WO | WO-07064895 A2 | 6/2007 |
| WO | WO-07106533 A1 | 9/2007 |
| WO | WO-07113818 A2 | 10/2007 |
| WO | WO-07113883 A1 | 10/2007 |
| WO | WO-07114860 A2 | 10/2007 |
| WO | WO-07118090 A2 | 10/2007 |
| WO | WO-07136850 A2 | 11/2007 |
| WO | WO-07136851 A2 | 11/2007 |
| WO | WO-08039982 A2 | 4/2008 |
| WO | WO-08083120 A2 | 7/2008 |
| WO | WO-08083235 A2 | 7/2008 |
| WO | WO-2009/017647 A1 | 2/2009 |
| WO | WO-09095920 A2 | 8/2009 |
| WO | WO-10/118126 A1 | 10/2010 |
| WO | WO-2012/017437 A1 | 2/2012 |
| WO | WO-2012/085907 A2 | 6/2012 |
| WO | WO-2013/035092 A2 | 3/2013 |
| WO | WO-2013/069020 A1 | 5/2013 |
| WO | WO-2013/164829 A1 | 11/2013 |

OTHER PUBLICATIONS

U.S. Appl. No. 60/721,728, filed Sep. 28, 2005.
U.S. Appl. No. 60/702,491, filed Jul. 25, 2005.
Evaluation of Cardiovascular Stents as Antennas for Implantable Wireless Applications, by Chow, IEEE Transactions on Microwave Theory and Techniques, vol. 57, No. 10, Oct. 2009.
Office Action dated Mar. 15, 2012, which issued during the prosecution of U.S. Appl. No. 12/792,227.
Office Action dated Aug. 9, 2011, which issued during the prosecution of U.S. Appl. No. 12/023,896.
Cardiovascular Stents as Antennas for Implantable Wireless Applications, by Ebrish, BMEN 5151, Apr. 29, 2010.
Office Action dated Mar. 3, 2012, which issued during the prosecution of U.S. Appl. No. 12/023,896.
Office Action dated Dec. 19, 2011, which issued during the prosecution of U.S. Appl. No. 11/995,904.
Office Action dated Nov. 18, 2009, which issued during the prosecution of U.S. Appl. No. 12/023,900.
International Search Report and Written Opinion dated Dec. 19, 2011, which issued during the prosecution of Applicant's PCT/IL2011/000636.
International Search Report dated Jan. 24, 2007, which issued during the prosecution of Applicant's PCT/IL06/00856.
International Search Report and Written Opinion dated May 12, 2009, which issued during the prosecution of Applicant's PCT/IL09/00115.
International Search Report and Written Opinion dated Jul. 13, 2009, which issued during the prosecution of Applicant's PCT/IL09/00117.
International Preliminary Report on Patentability dated Jan. 24, 2007, which issued during the prosecution of Applicant's PCT/IL06/00856.
International Preliminary Report on Patentability dated Aug. 3, 2010, which issued during the prosecution of Applicant's PCT/IL09/00117.
International Preliminary Report on Patentability dated Aug. 3, 2010, which issued during the prosecution of Applicant's PCT/IL09/00115.
Hamilton, Coronary vascular sympathetic beta-receptor innervations,, American Journal of Physiology, vol. 230, No. 6, Jun. 1976.
International Search Report and a Written Opinion dated Mar. 5, 2013, which issued during the prosecution of Applicant's PCT/IL12/00336.
Matheny, Vagus nerve stimulation as a method to temporarily slow or arrest the heart, Ann Thorac Surg. Jun. 1997;63(6 Suppl):S28-9. Abstract only.
Lewis, Vagus nerve stimulation decreases left ventricular contractility in vivo in the human and pig heart, J Physiol. Jul. 15, 2001; 534(Pt 2): 547-552.
Laitinen, Am J, Sympathovagal balance is major determinant of short-term blood pressure variability in healthy subjects, Physiol Heart Circ Physiol 276:1245-1252, 1999.
Frost MC, Preparation and characterization of implantable sensors with nitric oxide release coatings, Microchemical Journal vol. 74 Issue: 3, Jun. 2003 pp. 277-288.
Baudrie, Am J, Optimal frequency ranges for extracting information on cardiovascular autonomic control from the blood pressure and pulse interval spectrograms in mice, Physiol Regul Integr Comp Physiol 292: R904-R912, 2007.
Kugiyama K, Nitric oxide activity is deficient in spasm arteries of patients with coronary spastic angina, Circulation 94:266-272 (1996).
Malpas, Neural influences on cardiovascular variability: possibilities and pitfalls,, Am J Physiol Heart Circ Physiol 282: H6-H20, 2002.
Shin Jae Ho, "Improving the biocompatibility of in vivo sensors via nitric oxide release," Analyst, 2006, 131, 609-615.
Zhao et al., Loss of nitric oxide production in the coronary circulation after the development of dilated cardiomyopathy: a specific defect in the neural regulation of coronary blood flow, Clinical and Experimental Pharmacology and Physiology 23(8): 715-721 (1996).
Sherman et al., Blockade of nitric oxide synthesis reduces myocardial oxygen consumption in vivo, Circulation 95:1328-1334 (1997).
Schoenfisch et al., "Improving the thromboresistivity of chemical sensors via nitric oxide release: fabrication and in vivo evaluation of NO-releasing oxygen-sensing catheters", Anal. Chem., 72 (6), 1119-1126, 2000.
Paulus, "Beneficial effects of nitric oxide on cardiac diastolic function: the flip side of the coin", Heart Failure Review 5(4):337-344 (2000).
Web page relating to EndoSure® Wireless AAA Pressure Measurement System, manufactured by CardioMEMS, Inc. (downloaded on

(56) References Cited

OTHER PUBLICATIONS

Nov. 30, 2010 from: <http://www.cardiomems.com/content.asp?display=medical+mb&expand=ess>.

Cheetah Medical Inc. manufactures the Cheetah Reliant, Jan. 23, 2008.

SULZER IntarTeraputic Inc. manufactures the IntraCoil® Self-Expanding Peripheral Sent (IntraCoil® Sent), Jun. 28, 2002.

Hayashida et al., "Comparison of neurogenic contraction and relaxation in canine corpus cavernosum and penile artery and vein", J. Pharmacol. 72:231-240 (1996), p. 232 col. 2, para. 1; p. 238, col. 2, para 2.

Biosense Webster, Inc. (CA, USA) manufactures the LASSO 2515 Variable Circular Mapping Catheter, 2010.

Wustmann, "Effects of chronic baroreceptor stimulation on the autonomic cardiovascular regulation in patients with drug-resistant arterial hypertension", Hypertension 2009; 54;530-536.

Yao Sheng-Kun, "Endogenous and exogenous nitric oxide protect against intracoronary thrombosis and reclusion after thrombolysis" Circulation. 1995;92 pp. 1005-1010.

"Heart rate variability," by Task Force of the European Society of Cardiology and the North American Society of Pacing and Electrophysiology, European Heart Journal (1996) 17, 354-381.

Vallais, "Heart rate and vasomotor control during exercise", Proceedings of the 29th Annual International Conference of the IEEE EMBS, Cité Internationale, Lyon, France, Aug. 23-26, 2007.

Sabbah H et al., "Global left ventricular remodeling with the Acorn Cardiac Support Device: Hemodynamic and angiographic findings in dogs with heart failure" Heart Failure Reviews 10(2):109-115 (2005) first page.

Kass D., Eur Heart J. Nov. 1992;13 Suppl. E:57-64.

Steendijk et al., European Heart Journal (2004) 6 (Supplement D), D35-D42.

Suga et al., Am J Physiol. Jan. 1981; 240(1):H39-44.

Kong et al. "Tumour necrosis factor-$\alpha$ and its receptors in the beneficial effects of vagal stimulation after myocardial infarction in rats". Clin Exp Pharmacol Physiol. 2011; 38:300-6.

Uemura et al., "Early short-term vagal nerve stimulation attenuates cardiac remodeling after reperfused myocardial infarction". J Card Fail. Aug. 2010;16(8):689-99.

Katare et al. "Vagal nerve stimulation prevents reperfusion injury through inhibition of opening of mitochondrial permeability transition pore independent of the bradycardiac effect". J Thorac Cardiovasc Surg. Jan. 2009;137(1):223-31.

Kawada et al. "Vagal stimulation suppresses ischemia-induced myocardial interstitial myoglobin release". Life Sci. Sep. 26, 2008;83(13-14):490-5.

Uemura et al. "Efferent vagal nerve stimulation induces tissue inhibitor of metalloproteinase-1 in myocardial ischemia-reperfusion injury in rabbit". Am J Physiol Heart Circ Physiol. Oct. 2007;293(4):H2254-61.

Mioni et al. "Activation of an efferent cholinergic pathway produces strong protection against myocardial ischemia/reperfusion injury in rats". Crit Care Med. Nov. 2005;33(11):2621-8.

Office Action dated Jun. 19, 2012, which issued during the prosecution of U.S. Appl. No. 11/995,904.

Office Action dated Aug. 29, 2012, which issued during the prosecution of U.S. Appl. No. 12/792,227.

U.S. Appl. No. 61/331,453, filed May 5, 2010.

Office Action dated Aug. 1, 2012, which issued during the prosecution of U.S. Appl.n No. 12/957,799.

International Search Report and Written Opinion dated Jul. 5, 2012, which issued during the prosecution of Applicant's PCT/IL11/00952.

Notice of Allowance dated Sept 18, 2013, which issued during the prosecution of U.S. Appl. No. 13/210,778.

Office Action dated Oct. 2, 2012, which issued during the prosecution of U.S. Appl. No. 12/851,214.

Office Action dated Sep. 18, 2012, which issued during the prosecution of U.S. Appl. No. 12/023,896.

English Translation of an Office Action dated Oct. 8, 2012, which issued during the prosecution of Chinese Patent Application No. 200980111617.8.

Office Action dated Jul. 18, 2012, which issued during the prosecution of U.S. Appl. No. 13/210,778.

Office Action dated Mar. 12, 2013, which issued during the prosecution of U.S. Appl. No. 13/210,778.

Supplementary European search Report dated Dec. 14, 2012, which issued during the prosecution of European Patent Application No. 06766171.

Office Action dated Apr. 25, 2013, which issued during the prosecution of U.S. Appl. No. 11/995,904.

Office Action dated May 10, 2013, which issued during the prosecution of U.S. Appl. No. 12/023,896.

Office Action dated Apr. 5, 2013, which issued during the prosecution of U.S. Appl. No. 12/792,227.

Takahata, "Stentenna: A Micromachined Antenna Stent for Wireless Monitoring of Implantable Microsensors" Engineering in Med. and Biol. Soci, 2003. Proceedings of the 25th Annual Intern Conference of the IEEE Sep. 17-21, 2003.

U.S. Appl. No. 61/532,660, filed Sep. 9, 2011.

U.S. Appl. No. 61/183,319, filed Jun. 2, 2009.

Taylor, The unequal influences of the left and right vagi on the control of the heart and pulmonary artery in the rattlesnake, Crotalus durissus, The Journal of Experimental Biology 212, pp. 145-151, 2009.

An Office Action dated Dec. 13, 2013, which issued during the procesution of U.S. Appl. No. 13/294,062.

An Office Action dated Jan. 27, 2014, which issued during the prosecution of U.S. Appl. No. 12/023,896.

Extended European Search Report dated Oct. 31, 2013, which issued during the prosecution of European Application No. 11814203.3.

An Office Action dated Nov. 12, 2013, which issued during the prosecution of U.S. Appl. No. 11/995,904.

An Office Action dated Dec. 20, 2013, which issued during the prosecution of U.S. Appl. No. 12/792,227.

Hennig et al., "Analysis of Power Absorption by Human Tissue in Deeply Implantable Medical Sensor Transponders", pp. 407-420, Advanced Microwave Circuits and Systems, Published onlihe Apr. 1, 2010.

Gabriel et al., "The Dielectric Properties of Biological Tissues: II. Measurements in the frequency range 10 Hz to 20 GHz", Phys. Med. Biol. 41 (1996) pp. 2251-2269.

Office Action dated Jan. 5, 2015 issued during the prosecution of U.S. Appl. No. 12/959,126.

Office Action dated Jan. 15, 2015 issued during prosecution of U.S. Appl. No. 14/356,829.

PCT International Search Report and Written Opinion dated Apr. 16, 2015, issued on corresponding PCT International Application No. PCT/IL2014/50972 (16 pages).

Extended European Search Report dated Jun. 29, 2016, issued during the prosecution of European Patent Application No. 12830322.9. (8 pages).

Office Action dated Jan. 4, 2016, issued during the prosecution of U.S. Appl. No. 13/741,154 (11 pages).

Office Action dated May 22, 2015, issued during the prosecution of U.S. Appl. No. 13/741,154 (8 pages).

Office Action dated Nov. 7, 2014 issued during the prosecution of U.S. Appl. No. 13/741,154 (18 pages).

An Office Action dated May 16, 2018, which issued during the prosecution of U.S. Appl. No. 15/034.803.

An Office Action dated Sep. 12, 2018, which issued during the prosecution of U.S. Appl. No. 14/486,081.

An Office Action dated Aug. 7, 2019, which issued during the prosecution of U.S. Appl. No. 15/034,803.

\* cited by examiner

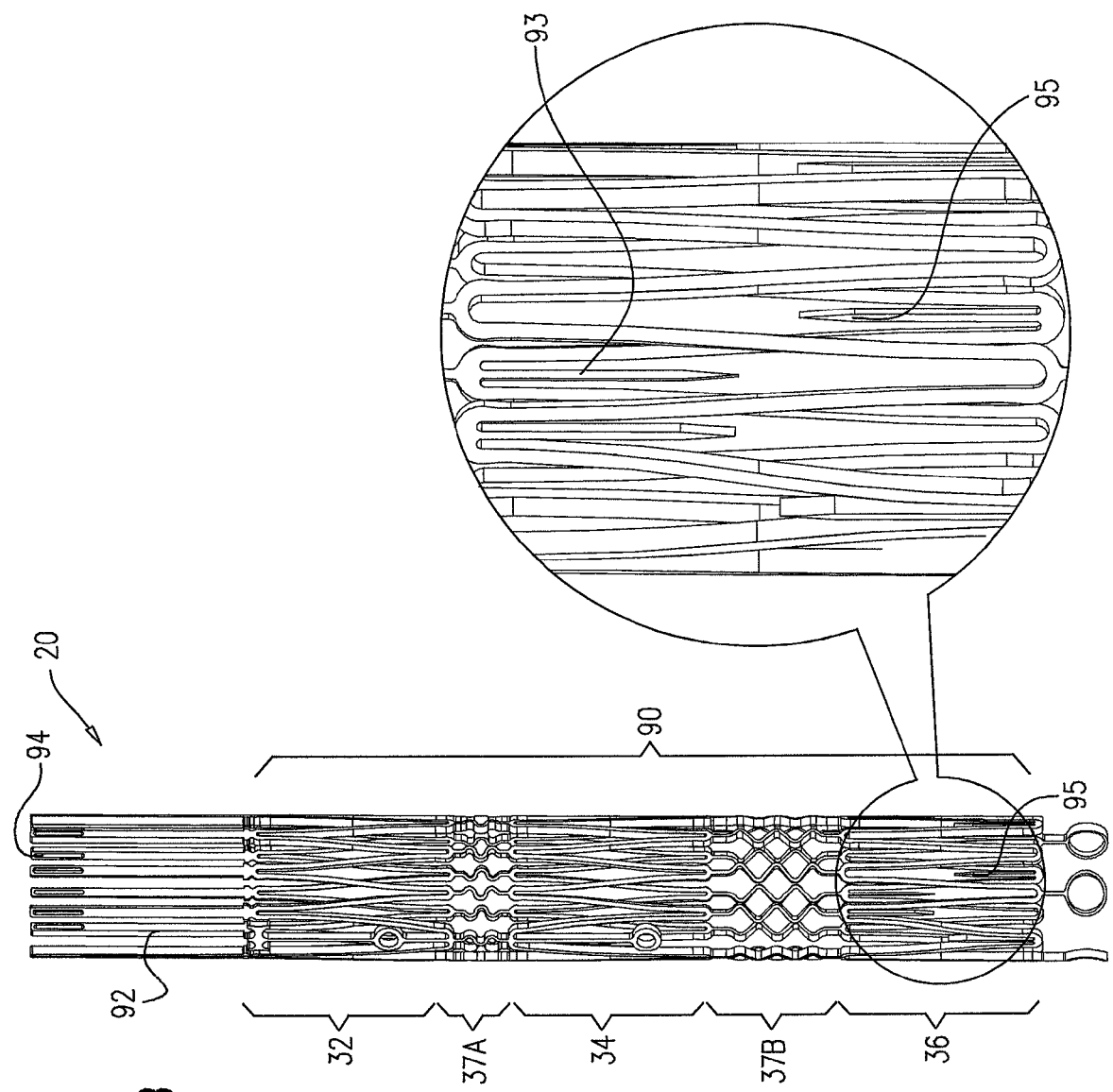

FIG. 7C
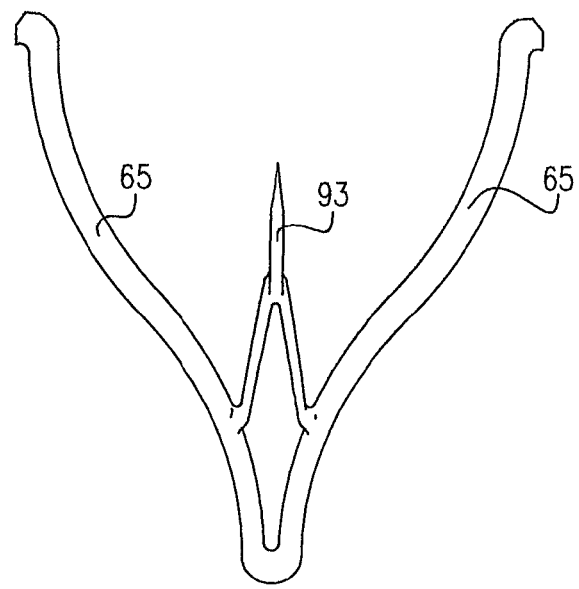
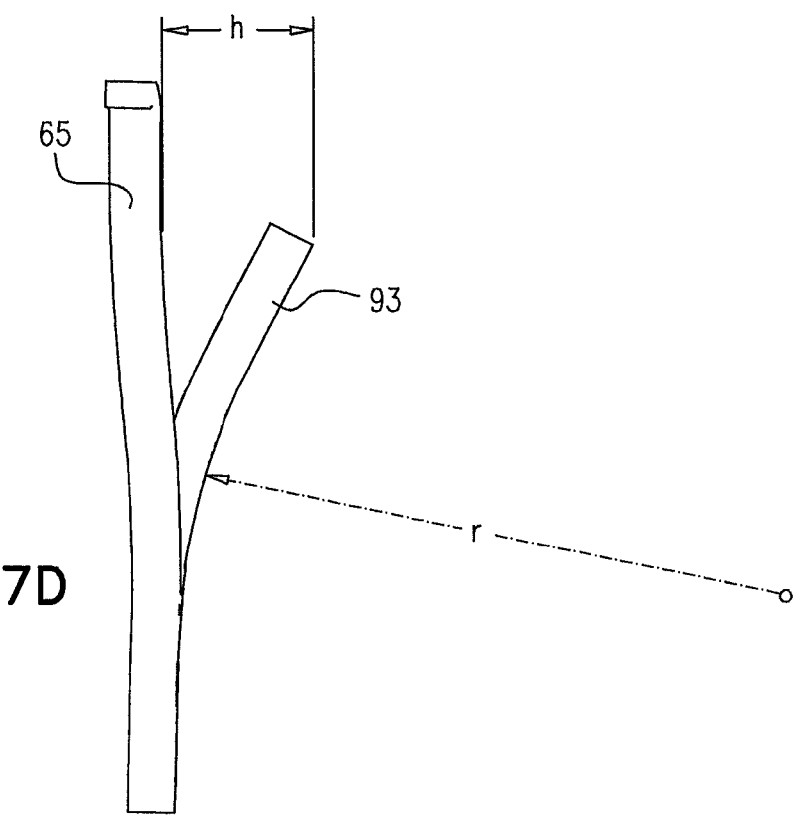
FIG. 7D

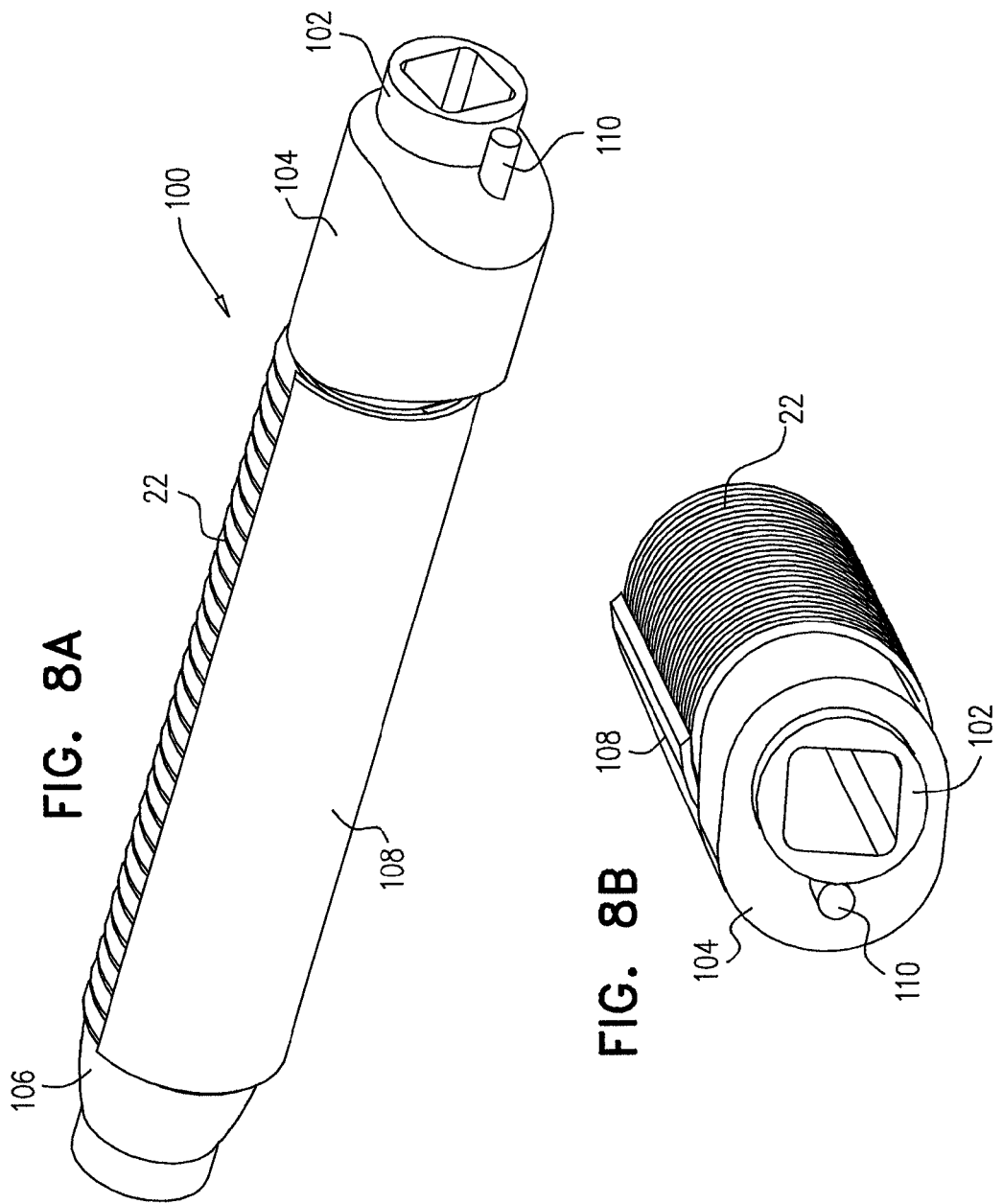

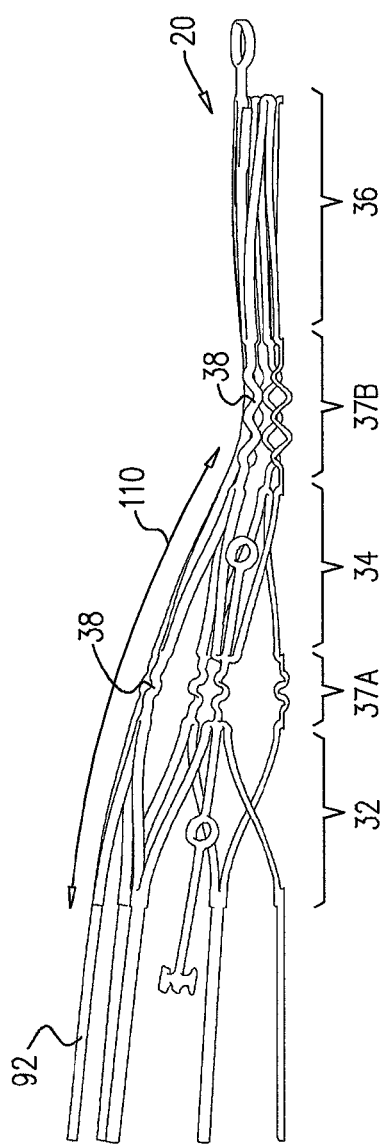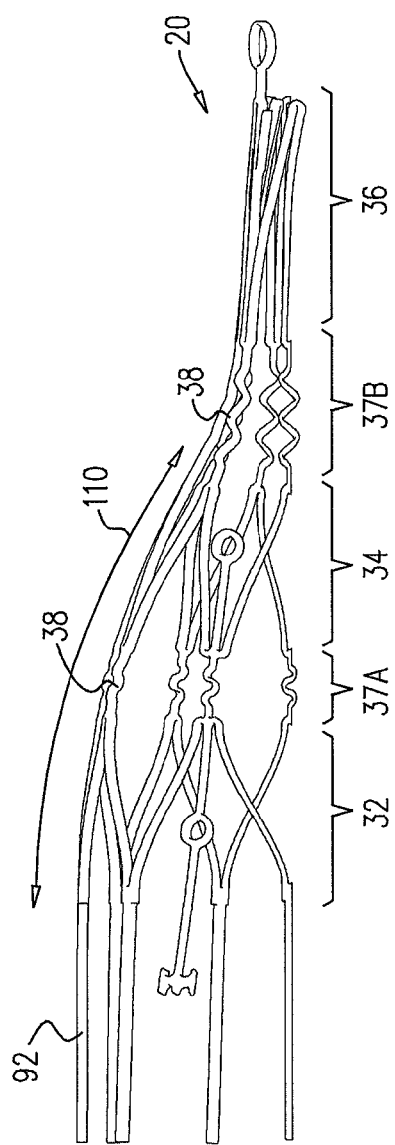

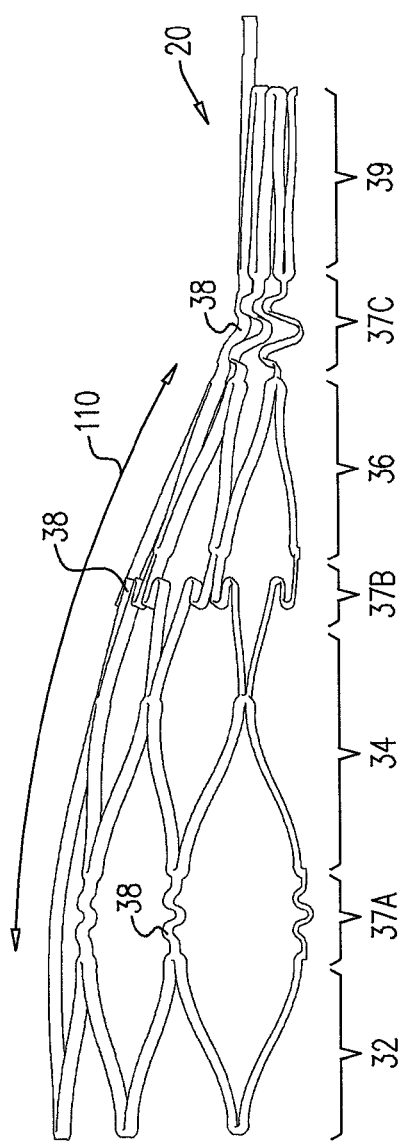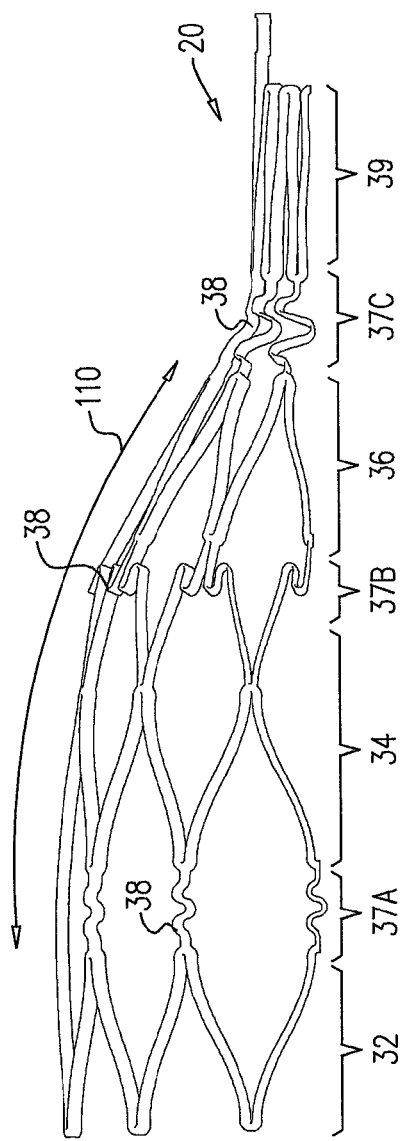

ANNULAR ANTENNA

CROSS-REFERENCES TO RELATED APPLICATIONS

The present application is a continuation of U.S. Ser. No. 13/741,154 to Dagan ( issued as U.S. Pat. No. 9,526,637 to Dagan), which is the U.S. national phase of International Application PCT/IL2012/000336 to Dagan (published as WO 13/035092), filed Sep. 09, 2012, which claims priority from U.S. Provisional Patent Application 61/532,660 to Dagan, filed Sept. 09, 2011, entitled, "Wireless endovascular stent-based electrodes."

The present application is related to U.S. Ser. No. 13/210,778 to Dagan (issued as U.S. Pat. No. 8,626,290), filed Aug. 16, 2011, which is a continuation-in-part of U.S. Ser. No. 12/957,799 to Gross (issued as U.S. Pat. No. 8,626,299), filed Dec. 1, 2010, entitled "Thoracic aorta and vagus nerve stimulation," which is a continuation-in-part of U.S. Ser. No. 12/792,227 to Gross (published as US 2010/0305392, now abandoned), filed Jun. 2, 2010, entitled "Thoracic aorta and vagus nerve stimulation," which claims the benefit of (a) U.S. Provisional Patent Application 61/183,319 to Reisner, filed Jun. 2, 2009, entitled "Thoracic aorta and vagus nerve stimulation," and (b) U.S. Provisional Patent Application 61/331,453 to Dagan, filed May 5, 2010, entitled "Thoracic aorta and vagus nerve stimulation."

All of the above-referenced applications are incorporated herein by reference.

FIELD OF EMBODIMENTS OF THE INVENTION

Some applications of the present invention generally relate to medical apparatus. Specifically, some applications of the present invention relate to stent-based electrodes for placement in a blood vessel.

BACKGROUND

Heart failure is a condition in which a problem with the structure or function of the heart impairs its ability to supply sufficient blood flow to meet the body's needs. The condition impairs quality of life and is a leading cause of hospitalizations and mortality in the western world. Treatment of heart failure is typically aimed at removal of precipitating causes, prevention of deterioration in cardiac function, and control of congestive state.

Hypertension, or chronic high blood pressure, is an extremely prevalent medical condition, which can lead to strokes, heart attacks, and heart failure. There are a variety of treatments that are available for treating hypertension, including lifestyle changes, and medication.

SUMMARY OF EMBODIMENTS

For some applications of the present invention, a stent is placed in a blood vessel. The stent defines at least first, second, and third strut portions disposed along the stent. The first and second strut portions are coupled to one another at a first junction that facilitates bending of the first and second strut portions with respect to one another, and the second and third strut portions are coupled to one another at a second junction that facilitates bending of the second and third strut portions with respect to one another. At least one electrode (typically, at least one pair of electrodes) is disposed on at least an outer surface of the stent. Typically, a current is driven into the blood vessel wall via the electrode.

Typically, the stent is inserted into the blood vessel via a delivery system, such as a catheter. For some applications, the junctions of the stent are configured to cause at least a portion of the outer surface of the stent to assume a convex profile upon protruding from catheter. For some applications, causing the outer surface of the stent to assume the convex profile reduces damage to the vessel wall that could be caused by the distal end of the stent contacting the vessel wall, relative to if the stent were to assume a straight profile upon protruding from the catheter. For some applications, the assumption of the convex profile by the outer surface of the stent brings the electrodes into contact with the vessel wall. For some applications, the junctions of the stent are configured to facilitate retrieval of the stent into the catheter.

It is noted that in the context of the present application, the terms "proximal" and "distal" are to be understood to be with respect to an access point of the stent into the subject's body. Thus, the distal end of the stent is the end of the stent that is further from the access point, and the proximal end of the stent is the end of the stent that is closest to the access point.

For some applications, the stent defines a stent body, and a plurality of posts that protrude longitudinally from a distal end of the stent body. An antenna is disposed annularly on distal portions of the posts, such that the posts separate the stent from the antenna. Typically, the stent electrode is powered via an inductive current that is generated in the antenna. Further typically, the posts, by separating the antenna from the stent body, facilitate an efficient transfer of electrical power to the antenna by reducing an inductive current that may be generated through the stent body and that may interfere with the inductive current in the antenna.

For some applications of the present invention, a stent is configured to be placed inside a subject's blood vessel (e.g., the subject's aorta, pulmonary artery, carotid artery, and/or renal artery), the stent being shaped to define at least one post. At least one coiled electrode is configured to be coupled to the stent by being placed on the post. An electrode-fixation member (e.g., a cap) is configured to fixedly couple the electrode to the post by being placed on the post.

There is therefore provided, in accordance with some applications of the present invention, apparatus for use with a blood vessel of a subject, including:

a stent configured to be placed in the blood vessel, the stent including:
  at least first, second, and third strut portions disposed along the stent,
  the first and second strut portions being coupled to one another at a first junction that facilitates bending of the first and second strut portions with respect to one another, and
  the second and third strut portions being coupled to one another at a second junction that facilitates bending of the second and third strut portions with respect to one another; and
at least one electrode disposed on at least an outer surface of the stent.

For some applications, the strut portions include portions of the stent that provide resistance against longitudinal compression of the stent, that permit radial compression of the stent, and that are less compliant than the junctions of the stent.

For some applications, the junctions include springs.

For some applications, the strut portions include struts that are made from a material selected from the group consisting of: a metal and an alloy, and the junctions include longitudinal locations along the stent body at which the struts of the stent are shaped such as to facilitate bending of the stent at those locations.

For some applications, the junctions are configured to act as joints around which the strut portions flex.

For some applications, the stent includes a fourth strut portion, the fourth strut portion being coupled to the third strut portion at a third junction that facilitates bending of the third and fourth strut portions with respect to one another.

For some applications, the blood vessel includes a curved blood vessel, and the junctions of the stent are configured to facilitate placing of the stent in the curved blood vessel, by facilitating bending of the strut portions of the stent with respect to one another.

For some applications, the stent is for use with a catheter, the stent is configured to be placed inside the blood vessel by being advanced out of a distal end of the catheter, and the junctions of the stent are configured to cause at least a portion of an outer surface of the stent to assume a convex profile upon protruding from catheter.

For some applications, the electrode is disposed on an outer surface of the stent, and, by causing at least the portion of the outer surface of the stent to assume the convex profile upon protruding from catheter, the junctions of the stent are configured to bring the electrode into contact with a wall of the blood vessel.

For some applications, by causing at least the portion of the outer surface of the stent to assume the convex profile upon protruding from catheter, the junctions of the stent are configured to cause an angle that the outer surface of the stent makes with a wall of the blood vessel, as the stent protrudes from the catheter, to be less than if the stent were to assume a straight profile upon protruding from the catheter.

For some applications, by causing the angle that the outer surface of the stent makes with a wall of the blood vessel as the stent protrudes from the catheter, to be less than if the stent were to assume a straight profile upon protruding from the catheter, the junctions are configured to reduce damage to the blood vessel wall.

For some applications, the stent is for use with a catheter, the stent is configured to be partially deployed inside the blood vessel by a distal portion of the stent being advanced out of a distal end of the catheter, and the junctions of the stent are configured, subsequent to the partial deployment of the stent, to facilitate retrieval of the stent into the catheter.

For some applications, the first junction of the stent is configured to facilitate retrieval of the stent into the catheter by allowing the first strut portion of the stent to radially expand, while the second strut portion remains substantially compressed inside the catheter.

For some applications, the second junction of the stent is configured to facilitate retrieval of the stent into the catheter by allowing the second strut portion of the stent to radially expand, while the third strut portion remains substantially compressed inside the catheter.

For some applications, the strut portions include struts that are made from a material selected from the group consisting of: a metal and an alloy, and the junctions include waved strips of the selected material.

For some applications, at least the first junction includes a waved strip of the selected material, the strip having a width of more than 0.1 mm.

For some applications, the strip has a width of less than 1 mm.

There is further provided, in accordance with some applications of the present invention, apparatus for use with a blood vessel of a subject, including:

a stent configured to be placed in the blood vessel, the stent including:
  a generally cylindrical stent body;
  a plurality of posts protruding longitudinally from an end of the stent body;
  an antenna disposed annularly on the posts, such that the posts separate the antenna from the end of the stent body.

For some applications, the apparatus further includes at least one coiled electrode, the coiled electrode being configured to be coupled to the stent by being placed on one of the posts.

For some applications, a length of each of the posts is greater than 1 mm.

For some applications, the length of each of the posts is greater than 5 mm.

For some applications, a length of each of the posts is less than 20 mm.

For some applications, the length of each of the posts is less than 15 mm.

For some applications, the antenna is configured to receive power by RF energy being transmitted toward the antenna, such as to generate an inductive current through the antenna.

For some applications, the posts are configured, by separating the antenna from the end of the stent body, to reduce a strength of the inductive current that is generated in the stent body, due to a magnetic field that is generated by the inductive current of the antenna.

For some applications, the posts are configured to provide electrical resistance, such that a current from the antenna to the stent body is negligible.

For some applications, the apparatus further includes a control capsule coupled to the stent, the control capsule being configured to be powered using the inductive current of the antenna.

For some applications, the apparatus further includes an electrode coupled to the stent, the control capsule being configured to drive a current into the blood vessel, via the electrode.

For some applications, the apparatus further includes an electrode coupled to the stent, the control capsule being configured to receive an electrical parameter of the blood vessel, via the electrode.

There is additionally provided, in accordance with some applications of the present invention, apparatus for use with a blood vessel of a subject, including:

an annular antenna configured to be placed inside the blood vessel such that radial expansion of the antenna is limited by a circumference of the blood vessel;
a transmitter configured to generate an inductive current in the antenna, by transmitting RF energy toward the antenna; and
a control unit configured to measure the inductive current in the antenna and, in response thereto, to determine a physiological parameter of the subject.

For some applications, the annular antenna includes at least a portion of a stent.

For some applications, the apparatus further includes a stent, the antenna being coupled to the stent.

For some applications, the control unit is configured to determine the physiological parameter of the subject by determining a parameter of the subject selected from the group consisting of: cardiac rate, respiratory rate, blood pressure, and blood vessel pulsation.

For some applications, the control unit is configured to determine the physiological parameter of the subject by interpreting variations in the inductive current that are measured at the antenna as being caused by variations in geometry of the antenna over the course of the subject's cardiac cycle.

For some applications, the control unit is configured to determine the physiological parameter of the subject by determining a respiratory cycle of the subject by analyzing an envelope of a variation of the inductive current with time.

For some applications, the transmitter is configured to transmit the RF energy at a frequency of more than 50 kHz.

For some applications, the transmitter is configured to transmit the RF energy at a frequency of more than 90 kHz.

For some applications, the transmitter is configured to transmit the RF energy at a frequency of less than 100 MHz.

For some applications, the transmitter is configured to transmit the RF energy at a frequency of more than 60 MHz.

There is further provided, in accordance with some applications of the present invention, a method for use with a blood vessel of a subject, including:
providing:
a stent that includes:
at least first, second, and third strut portions disposed along the stent,
the first and second strut portions being coupled to one another at a first junction that facilitates bending of the first and second strut portions with respect to one another, and
the second and third strut portions being coupled to one another at a second junction that facilitates bending of the second and third strut portions with respect to one another; and
at least one electrode disposed on at least an outer surface of the stent; and
placing the stent and the electrode inside the blood vessel.

There is further provided, in accordance with some applications of the present invention, a method for use with a blood vessel of a subject, including:
providing a stent that includes:
a generally cylindrical stent body;
a plurality of posts longitudinally protruding from an end of the stent body;
an antenna disposed annularly on the posts, such that the posts separate the antenna from the end of the stent body; and
placing the stent inside the blood vessel.

There is additionally provided, in accordance with some applications of the present invention, a method for use with a blood vessel of a subject, comprising:
placing into the blood vessel:
a stent having a generally cylindrical stent body;
at least one electrode that is coupled to the stent body; and
an antenna that is coupled to the stent body,
the placing being performed such that the antenna is separated from the stent body; and
operating a transmitter:
to generate an inductive current through the antenna by transmitting RF energy toward the antenna; and
using the inductive current, to drive a current into the blood vessel via the electrode.

For some applications, placing the stent and the antenna into the blood vessel includes reducing a strength of the inductive current that is generated in the stent body, due to a magnetic field that is generated by the antenna, by placing the stent and the antenna such that the antenna is separated from the stent body.

For some applications, placing the stent and the antenna into the blood vessel includes placing the stent and the antenna into the blood vessel such that the stent body is separated from the antenna by a distance that is greater than 1 mm.

For some applications, placing the stent and the antenna into the blood vessel includes placing the stent and the antenna into the blood vessel such that the stent body is separated from the antenna by a distance that is greater than 5 mm.

For some applications, placing the stent and the antenna into the blood vessel includes placing the stent and the antenna into the blood vessel such that the stent body is separated from the antenna by a distance that is less than 20 mm.

For some applications, placing the stent and the antenna into the blood vessel includes placing the stent and the antenna into the blood vessel such that the stent body is separated from the antenna by a distance that is less than 15 mm.

There is further provided, in accordance with some applications of the present invention, a method for use with an annular antenna that has been placed in a blood vessel and allowed to expand radially, such that radial expansion of the antenna is limited by a circumference of the blood vessel, the method comprising:
generating an inductive current in the antenna, by transmitting RF energy toward the antenna;
measuring the inductive current in the antenna; and
in response thereto, determining a physiological parameter of the subject.

There is further provided, in accordance with some applications of the present invention, apparatus, including:
a stent shaped to define struts and at least one post;
a coiled electrode configured to be coupled to the stent by being placed on the post; and
an electrode-fixation member configured to fixedly couple the coiled electrode to the post by being placed on the post.

The present invention will be more fully understood from the following detailed description of embodiments thereof, taken together with the drawings, in which:

BRIEF DESCRIPTION OF THE DRAWINGS

FIGS. 7A-B are schematic illustrations of a stent that defines a stent body with posts protruding from a distal end of the stent body, in accordance with some additional applications of the present invention;

FIGS. 7C-D are schematic illustrations of a barb of a stent, in accordance with some applications of the present invention;

FIGS. 8A-B are schematic illustrations of a construction for coupling a coiled electrode to a post of a stent, in accordance with some applications of the present invention;

FIGS. 9A-E are schematic illustration of respective steps of the opening of a stent that defines two junctions, in accordance with some applications of the present invention;

FIGS. 10A-E are schematic illustration of respective steps of the opening of a stent that defines three junctions, in accordance with some applications of the present invention;

DETAILED DESCRIPTION OF EMBODIMENTS

Figure 1:
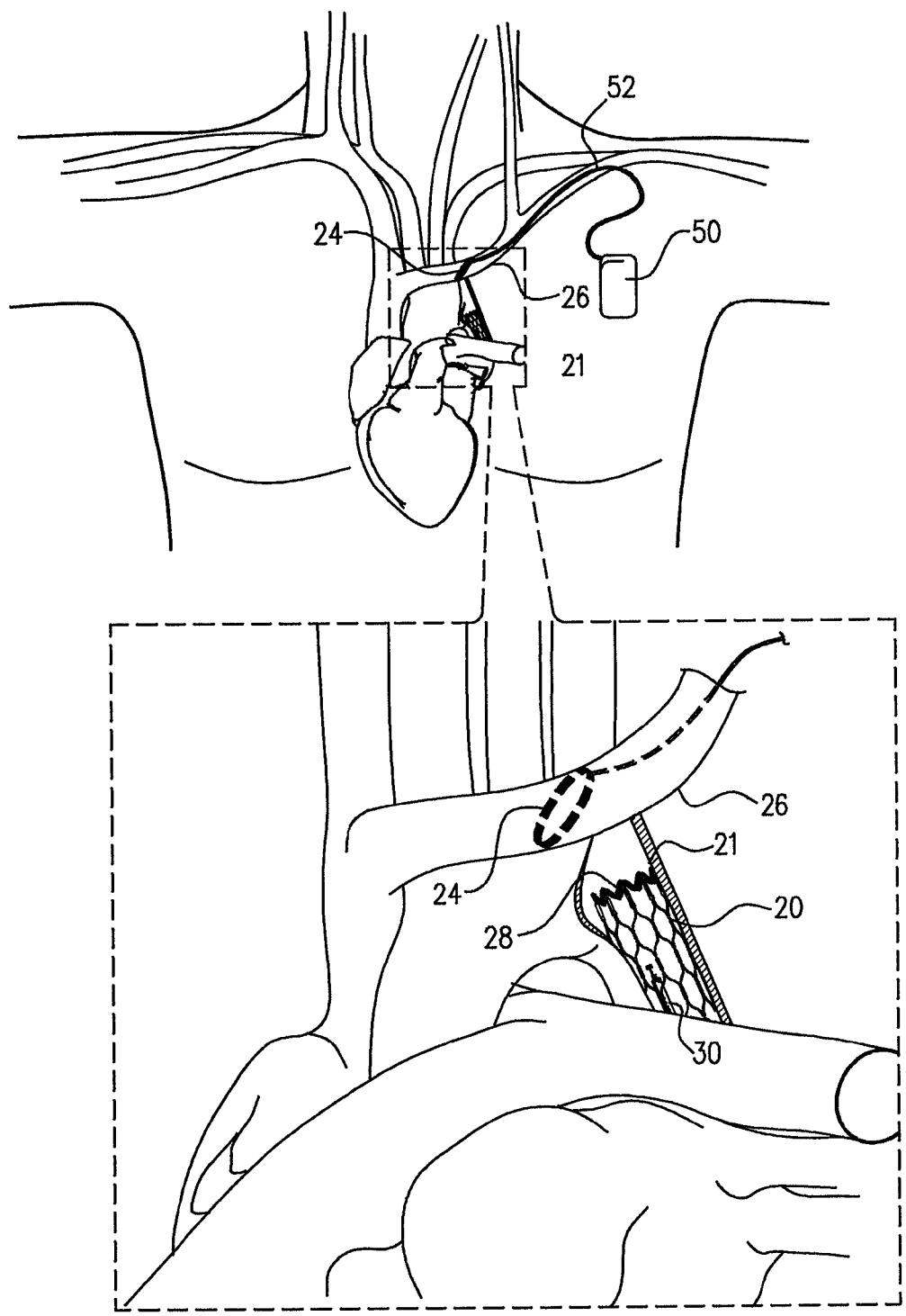
FIG. 1 is schematic illustrations of a stent placed inside a subject's aorta, electrodes being disposed on the stent, in accordance with some applications of the present invention.
Figure 2A:
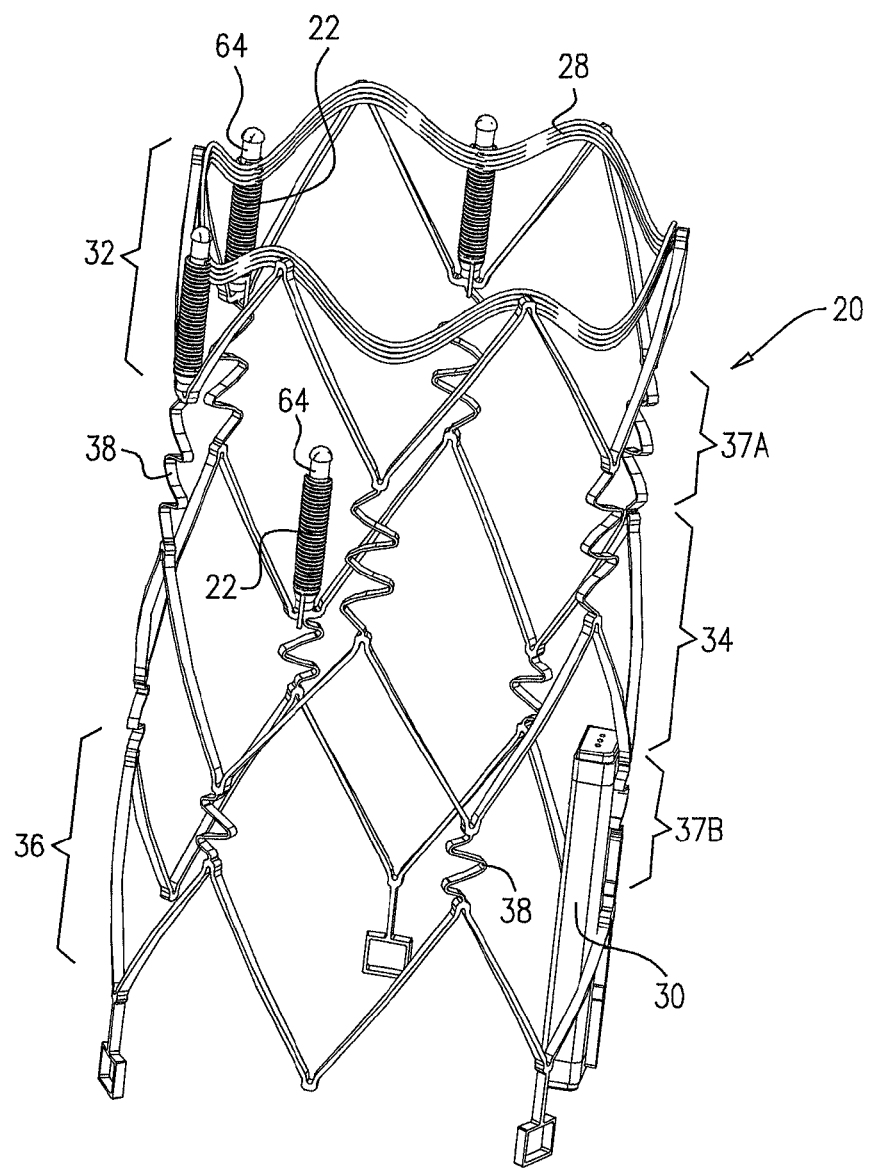
FIGS. 2A-C are schematic illustrations of a stent, in accordance with respective applications of the present invention.

Reference is now made to FIG. 1, which is a schematic illustration of a stent 20 placed inside a subject's blood vessel 21, at least one electrode 22 (FIG. 2A), and typically, a plurality of electrodes, being disposed on the stent, in accordance with some applications of the present invention. Reference is also made to FIG. 2A, which is a schematic illustration of the stent in the absence of the subject's anatomy, in accordance with some applications of the present invention.

It is noted that FIG. 1 shows stent 20 disposed inside the subject's aorta. However, the scope of the present invention includes placing the stent in any blood vessel of the subject, e.g., the subject's carotid artery, pulmonary artery, and/or renal artery. For example, the stent may be placed in the renal artery, in order to treat renal dysfunction, and/or in the pulmonary artery, in order to treat pulmonary hypertension. Alternatively or additionally, the stent may be placed in the pulmonary artery and/or the carotid artery in order to be used for vagal stimulation (e.g., vasovagal stimulation), for example, in order to treat gastroesophageal reflux disease (GERD).

Similarly, although FIG. 1 shows a portion of the stent disposed in the aortic arch, and a portion of the stent disposed in the descending aorta, the scope of the present invention includes placing the stent at any location within the aorta, such as in the ascending aorta, the descending aorta, the aortic arch, or a combination thereof.

For some applications, electrodes 22 are placed in contact with an aortic site, which is typically as described in U.S. Ser. No. 13/210,778 (published as US 2012/0035679), U.S. Ser. No. 12/957,799 to Gross (published as US 2011/0137370), and/or U.S. Ser. No. 12/792,227 to Gross (published as US 2010/0305392), all of which applications are incorporated herein by reference. Thus, the aortic site is typically between the bifurcation of the aorta with the left subclavian artery and the bifurcation of the aorta with the fifth intercostal artery. Further typically, the aortic site is between the bifurcation of the aorta with the left subclavian artery and the bifurcation of the aorta with the fourth intercostal artery, e.g., between the bifurcation of the aorta with the left subclavian artery and the bifurcation of the aorta with the first intercostal artery. For some applications, the aortic site is between the bifurcations of the aorta with the first and fifth intercostal arteries.

For some applications, a current is driven into the subject's aorta, e.g., in order to treat the subject for a condition such as congestive heart failure, diastolic heart failure, and/or hypertension, e.g., as described in as described in U.S. Ser. No. 13/210,778 (published as US 2012/0035679), U.S. Ser. No. 12/957,799 to Gross (published as US 2011/0137370), and/or U.S. Ser. No. 12/792,227 to Gross (published as US 2010/0305392), all of which applications are incorporated herein by reference. For some applications, the subject's cardiac cycle is determined by detecting an electrical signal from the subject's aorta, via electrodes 22, and deriving the subject's ECG and/or blood pressure from the electrical signal detected at the aorta, e.g., in accordance with techniques described in U.S. Ser. No. 12/792,227 to Gross (published as US 2010/0305392). For some applications, electrical stimulation is applied to the aorta in coordination with the subject's cardiac cycle, based upon the electrical signal detected at the aorta.

For some applications, electrodes are placed at a different location (e.g., a different location within the aorta, or within a different blood vessel of the subject, as described hereinabove), and a current is driven into the different location via the electrodes, or an electrical signal is detected from the different location via the electrodes. For example, a current may be driven into the different location in order to treat the subject for congestive heart failure, and/or hypertension.

Typically, the compliance of stent 20 varies along the length of the stent. For some applications, the compliance of the stent varies along the length of the stent in a manner that conforms with local stresses exerted on the stent by collagen fibers of the blood vessel. For some applications, the compliance of the stent varies along the length of the stent in a manner that facilitates placement of the stent in a curved blood vessel, the stent being configured to conform with the local shape of the blood vessel.

Typically, stent 20 includes a plurality of strut portions along the length of the stent, and the strut portions are coupled to each other at junctions 37, for example, junctions that include springs 38. Typically, the compliance of the stent at the junctions is greater than the compliance of the stent at the strut portions. For some applications, the stent is configured to be placed in a curved blood vessel. For some applications, the compliance of the stent at the junctions facilitates curvature of the stent that conforms with the curvature of the blood vessel. For example, the compliance of the stent at the junctions may facilitate curvature of the stent such that local longitudinal axes of respective strut portions of the stent are aligned with local longitudinal axes of a curved blood vessel. For some applications, the compliance of the stent at the junctions provides flexibility to the stent while the stent is being advanced through a delivery system (such as a catheter).

For example, with reference to FIG. 2A, in order to facilitate placement of electrodes 22 at an aortic site as described hereinabove, a first strut portion 32 (e.g., a first row of struts) of stent 20 is placed at the aortic arch, and a second strut portion 34 (e.g., a second row of struts) of the stent is placed in the descending aorta. Alternatively, the second portion is placed in a portion of the aortic arch that is downstream of the aortic arch with respect to the first portion. Upon placement of the first and second portions within the aorta as described, the local longitudinal axis of the first portion of the stent is disposed at an angle from that of the second portion of the stent. As described hereinabove, in order to facilitate placement of the stent such that the positions of the first and second portions of the stent are as described, the stent defines a junction 37A, e.g., a junction that include springs 38, configured to facilitate bending of the stent, between the first and second portions of the stent. Thus, the junctions act as joints that facilitate bending of the strut portions with respect to one another about the joints. For some applications, the stent defines additional junctions, e.g., additional springs, between other portions of the stent. For example (as shown in FIG. 2), the stent may define a third strut portion 36 (e.g., a third row of struts) configured to be placed downstream of the second portion, a control capsule 30 being coupled to the third portion. Springs 38 disposed at junction 37B, between the second and third strut portions of the stent, facilitate bending of the stent between the second and third portions. Thus, springs 38, disposed between the second and third strut portions of the stent, act as a joint that facilitates bending between the second and third strut portions.

It is noted that in the context of the present application, the term "spring" should not necessarily be understood to be limited to denoting an object having a particular shape. Rather, the term "spring" should be understood to denote a portion of the stent that stores potential energy when it is bent and releases it when the restraining force is removed. It is further noted that, in FIG. 2A, the junctions at which the strut portions of stent 20 are connected to one another are shown as being formed as waved strips that act as springs. However, the scope of the present inventions includes using other elements at the junctions, in order to facilitate bending of the strut portions with respect to one another. For example, the struts of the stent at the junctions may be shaped such that the compliance of the stent at the junctions is greater than the compliance of the stent at the strut portions, as described hereinbelow with reference to FIG. 7E. Alternatively or additionally, the junctions may be shaped as joints at which pairs of struts of the stent are coupled to each other by sinusoidally shaped strips, such as junction 37B of stent 20 as shown in FIG. 2C.

Stent 20 is typically configured to be placed inside the blood vessel (e.g., the aorta) percutaneously using a delivery system, e.g., using a 12 Fr-20 Fr catheter (e.g., a 16 Fr catheter). Typically, upon being placed inside the blood vessel, the stent is partially deployed, such that (a) electrodes 22 contact the wall of the blood vessel at a given location within the blood vessel, and (b) a proximal portion of the stent is disposed inside the catheter, such that the stent may be retrieved into the catheter. The response of the subject to electrical stimulation of the blood vessel at the current location of the electrodes within the blood vessel is determined. In response thereto, the stent is (a) fully deployed at the current location of the stent (b) retrieved into the catheter and redeployed at a different location within the blood vessel, or (c) retrieved into the catheter and removed from the subject's body (e.g., if the subject does not respond in a suitable manner to electrical stimulation of the blood vessel at any locations at which the stent is deployed). For some applications, the junctions of the stent facilitate the partial deployment of the stent such that (a) electrodes 22 contact the wall of the blood vessel at a given location within the blood vessel, and (b) a proximal portion of the stent is disposed inside the catheter, such that the stent may be retrieved into the catheter, as described in further detail below with reference to FIGS. 9A-E and 10A-E.

Typically, the compliance of stent 20 is such that pulsation of the blood vessel is substantially maintained upon the stent being deployed inside the blood vessel. Further typically, the stent and components coupled thereto (such as control capsule 30) are shaped such as to substantially maintain blood flow through the blood vessel upon deployment of the stent inside the blood vessel.

For some applications, stent 20 is cut from a nitinol tube (or a tube made from a different material, such as stainless steel) having a wall thickness of more than 0.3 mm (e.g., more than 0.4 mm), and/or less than 0.7 mm (e.g., less than 0.6 mm). For some applications the length of the stent is more than 25 mm (e.g., more than 30 mm), and/or less than 100 mm (e.g., less than 40 mm) For some applications, the stent has an outer diameter of more than 10 mm (e.g., more than 15 mm), and/or less than 35 mm (e.g., less than 25 mm). Typically, the stent has a crimped profile of less than 18 Fr (e.g., 12 Fr or less), and/or more than 8 Fr (e.g., 10 Fr or more).

For some applications, a transmitter 24 (FIG. 1) is placed in a vein 26 that is in the vicinity of the blood vessel in which the stent is placed, e.g., in accordance with techniques described in U.S. Ser. No. 12/957,799 to Gross (published as US 2011/0137370), which is incorporated herein by reference. A signal and/or power is typically transmitted to the electrodes by the transmitter that drives the electrodes to drive a current into the subject's blood vessel. An antenna 28 that is disposed on stent 20 receives the signal, and control capsule 30 that is disposed on the stent drives the electrodes to drive the current into the blood vessel, in response to the antenna receiving the signal. For some applications, a different type of transmitter from transmitter 24, shown in FIG. 1, is used to transmit a signal and/or power toward antenna 28.

For some applications, one or more portions of stent 20 function as antenna 28. For example, the stent may be cut from a nitinol tube and a portion of the tube functions as the antenna. Alternatively, an antenna may be coupled to the stent, e.g., using techniques described herein. For some applications, the diameter of the blood vessel at the antenna and/or hemodynamic parameters are measured using the antenna, as described in further detail hereinbelow, with reference to FIGS. 11-12.

For some applications, capsule 30 is coupled to the stent mechanically, e.g., using a locking mechanism, adhesive (e.g., epoxy), suturing, and/or by pressing the capsule against struts of the stent, such that the capsule becomes coupled to the stent by deforming to conform with the shape of the stent struts. For some applications, the capsule is coupled to a fabric sleeve (e.g., by being printed onto the sleeve) and the sleeve is coupled (e.g., sutured) to the stent, e.g., as described hereinbelow.

For some applications, a control unit for driving electrode 22 is disposed in a subcutaneously implanted housing 50. The control unit is coupled, via a lead 52 to transmitter 24

(e.g., a transmitting coil, as shown) that is implanted in vein 26 that is in the vicinity of the blood vessel (e.g., the aorta). For example, the transmitter may be placed in the innominate vein (also called the left brachiocephalic vein), placement of the transmitter in the innominate vein being performed via the left subclavian vein. The control unit wirelessly drives the electrodes, receives a signal from the electrode, and/or powers circuitry associated with the electrode (e.g., circuitry of control capsule 30) by transmitting a wireless signal to antenna 28, via transmitter 24. Typically, the transmitter is placed inside the vein such that it is at a distance from the intra-arterial electrodes of more than 2 cm and/or less than 5 cm (e.g., 2-5 cm), or more than 5 cm and/or less than 20 cm (e.g., 5-20 cm). For example, the transmitter may be placed in the pulmonary vein, innominate vein, vena cava, jugular vein, and/or subclavian vein.

For some applications, housing 50 which houses the control unit is implanted (e.g., implanted subcutaneously) in the vicinity of electrode 22, e.g., within 10 cm of the electrode. For some applications, housing 50 is disposed on a chest belt that is worn on the subject's chest, such that the housing is outside the subject's body, but within 15 cm of the electrode. The control unit wirelessly drives the electrode, receives a signal from the electrode, and/or powers circuitry associated with the electrode (e.g., circuitry of control capsule 30), by transmitting a wireless signal to antenna 28.

For some applications, the control unit is disposed inside housing 50 and is implanted subcutaneously inside the subject, as described hereinabove. Parameters of the control unit may be adjusted by transmitting a signal to the control unit from outside the subject's body. Alternatively or additionally, electrical power may be supplied to the subcutaneously implanted control unit, by transmitting a signal to the control unit from outside the subject's body.

For some applications, transmitter 24 is mounted on a support structure (such as a nitinol ring) in order to orient the transmitter in a suitable orientation for transmitting a signal to antenna 28, which is coupled to the electrode. For example, the transmitter may include a coil that is mounted on the support structure such that a plane that is defined by the coil is at an angle of greater than 10 degrees from a plane that is perpendicular to the local longitudinal axis of the vein in which the transmitter is placed. Alternatively, the transmitter coil is oriented with respect to the support structure such that the plane defined by the coil is generally perpendicular to the local longitudinal axis of the vein.

For some applications, transmitter coil 24 is placed inside the vein such that the plane defined by the coil is at an angle of greater than 10 degrees from a plane that is perpendicular to the local longitudinal axis of the vein, without mounting the coil on a support structure. Alternatively, the coil is placed inside the vein such that the plane defined by the coil is generally perpendicular to the local longitudinal axis of the vein, without mounting the coil on a support structure. Typically, the transmitter coil is placed in the vein (by being mounted on a support structure, or not by being mounted on a support structure) such that the plane defined by the transmitter coil is generally perpendicular to the plane defined by antenna 28, which is placed in the subject's artery.

Figure 2B:
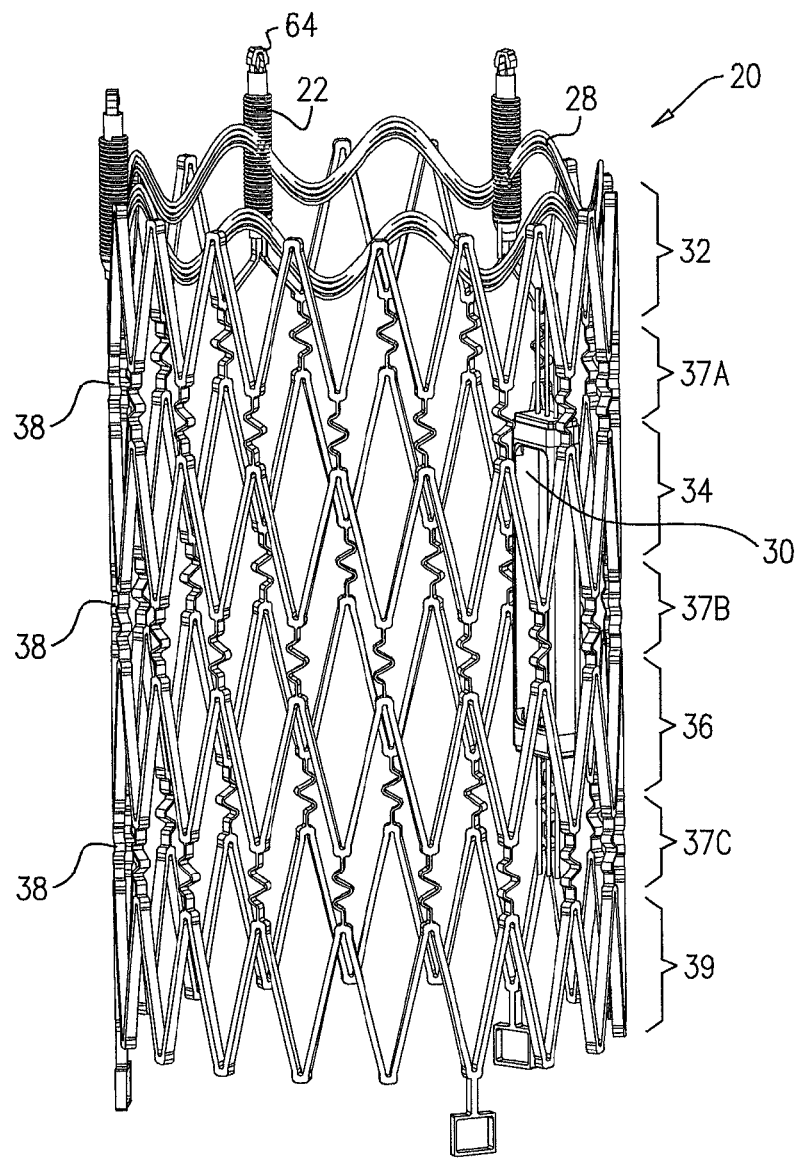
Figure 2C:
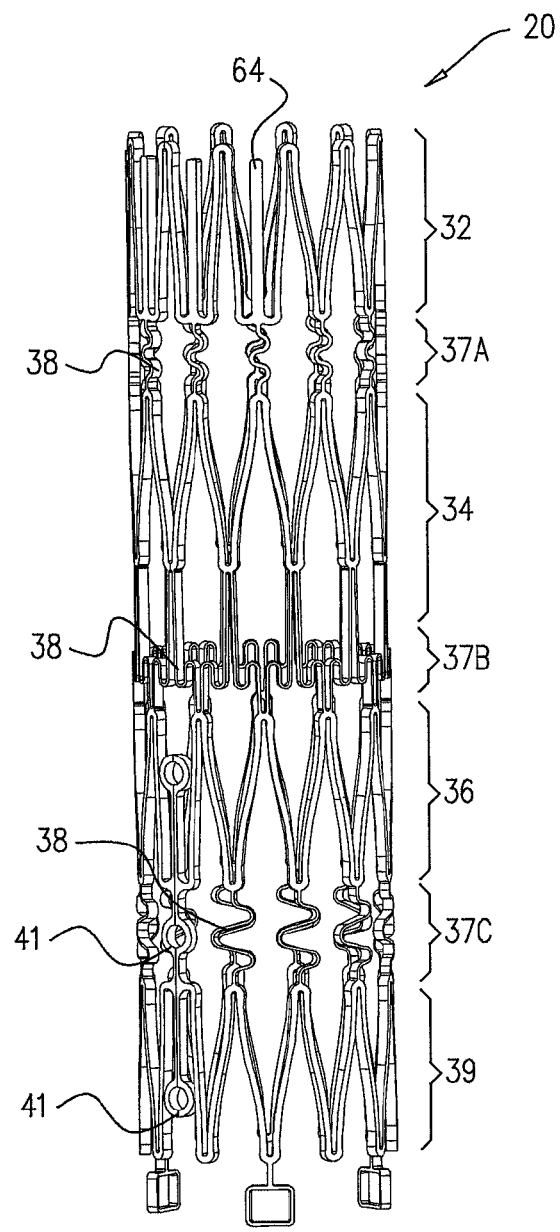

Reference is now made to FIGS. 2B-C, which are schematic illustrations of stent 20, in accordance with respective applications of the present invention.

FIGS. 2B-C are schematic illustrations of respective stents that define three junctions 37, in accordance with respective applications of the present invention. The stents shown in FIGS. 2B and FIG. 2C differ from one another in that (a) springs 38 of second junction 37B of the spring shown in FIG. 2C are a different shape from the springs of the second junction of the stent shown in FIG. 2B, and (b) the shapes of the struts of the strut portions of the respective stents are different. In all other aspects, the stents shown in FIGS. 2B and 2C are generally similar to one another.

Stent 20 as shown in FIGS. 2B and 2C includes first strut portion 32 and second strut portion 34 that are coupled to one another at first junction 37A, the first junction being configured to facilitate bending of the first strut portion with respect to the second strut portion, such that the local longitudinal axis of the first strut portion of the stent may be disposed at an angle from that of the second strut portion of the stent. The stent additionally includes third strut portion 36 coupled to second strut portion at second junction 37B, the second junction being configured to facilitate bending of the second strut portion with respect to the third strut portion, such that the local longitudinal axis of the second strut portion of the stent may be disposed at an angle from that of the third strut portion of the stent. The stent further includes fourth strut portion 39 coupled to third strut portion at third junction 37C, the third junction being configured to facilitate bending of the third strut portion with respect to the second strut portion, such that the local longitudinal axis of the third strut portion of the stent may be disposed at an angle from that of the fourth strut portion of the stent.

For some applications, the first, second and third junctions of the stent facilitate the partial deployment of the stent such that (a) electrodes 22 contact the wall of the blood vessel at a given location within the blood vessel, and (b) a proximal portion of the stent is disposed inside the catheter, such that the stent may be retrieved into the catheter, as described in further detail below with reference to FIGS. 10A-E. Stent 20 as shown in FIGS. 2B-C is generally similar to stent 20 as shown in FIG. 2A except that (a) stent 20 as shown in FIGS. 2B-C defines an additional strut portion, and a corresponding additional junction as compared with stent 20 of FIG. 2A, and (b) stent 20 as shown in FIGS. 2B-C only has posts 64 (to which coiled electrodes 22 are couplable) on the first strut portion of the stent, whereas stent 20 as shown in FIG. 2A has posts 64 coupled to the first and second strut portions.

It is noted that for some applications, a stent having more than three junctions (and correspondingly, more than four strut portions) is used. Typically, the number of junctions that the stent defines increases as the length of the stent increases. For some applications, the length of the stent that is used increases as the diameter of the vessel in which the stent is to be placed increases, in order to facilitate greater radial expansion of the distal end of the stent during partial deployment of the stent. In addition, the length of the stent that is used increases as the curvature of the vessel in which the stent is to be placed increases, in order to facilitate greater radial expansion of the distal end of the stent during partial deployment of the stent. In a curved vessel, it may be necessary to radially expand the stent to a greater diameter than is necessary in a similar sized straight vessel, in order to bring the electrodes into contact with a portion of the vessel wall that is curving away from the distal end of the delivery system. Furthermore, in a curved vessel, the distal end of the delivery system (e.g., the catheter), via which the stent is inserted, is typically disposed closer to the wall on one side of the vessel, and is not disposed in the center of the vessel, due to the delivery system distal end (e.g., the catheter tip) typically being substantially straight, and the vessel being curved. Therefore, in a curved vessel, it may be necessary to radially expand the stent to a greater diameter than is necessary in a similar sized straight vessel, in order to bring the electrodes into contact with the wall that is further from the distal end of the delivery system.

Figure 7A:
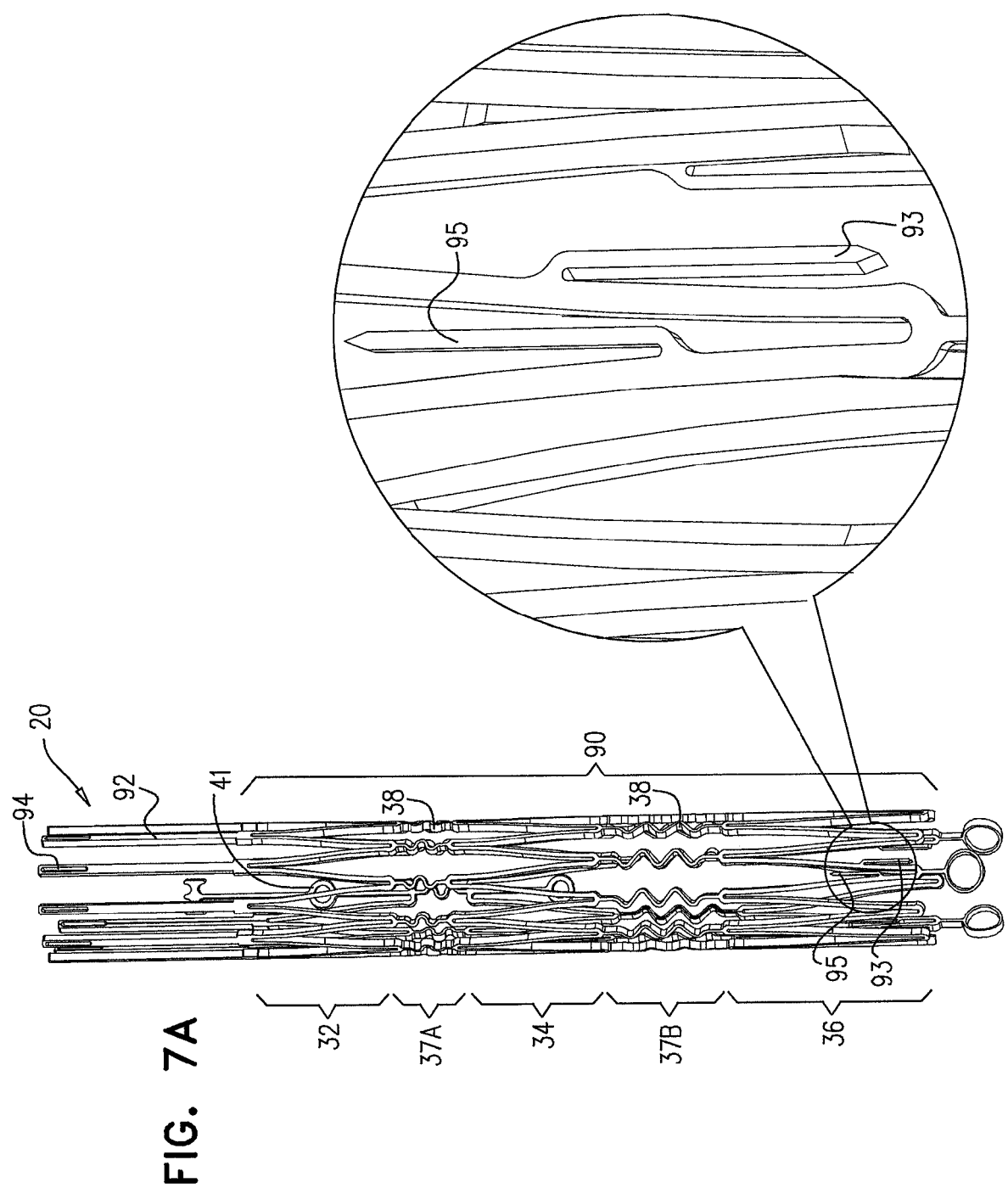

As shown in FIG. 2C, stent 20 typically defines coupling elements 41 (e.g., holes) for facilitating coupling of control capsule 30 to the stent. Although in FIG. 2C, the coupling elements are shown as being disposed on the proximal half of the stent, for some applications, the coupling elements are disposed on the distal half of the stent, e.g., as shown in FIG. 7A.

Figure 3A:
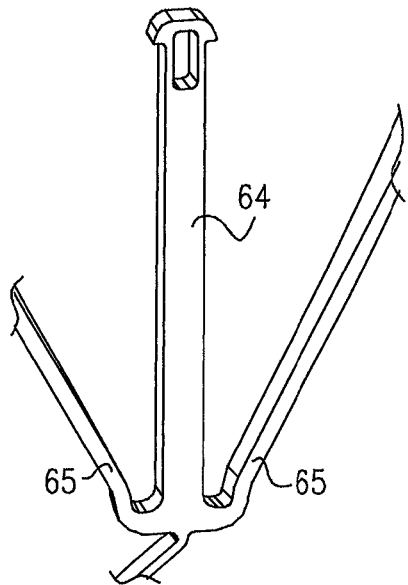
FIG. 3A is a schematic illustration of a post of a stent, in accordance with some applications of the present invention.
Figure 3B:
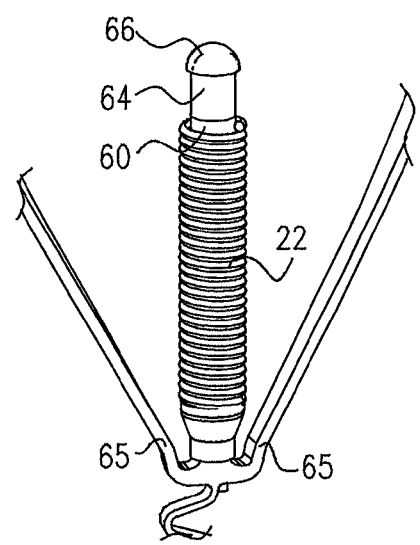
FIG. 3B is a schematic illustration of a coiled electrode disposed on a post of a stent, in accordance with some applications of the present invention.

Reference is now made to FIG. 3A, which is a schematic illustration of a post 64 that is defined by stent 20, in accordance with some applications of the present invention. Reference is also made to FIG. 3B, which is a schematic illustration of electrode 22 coupled to stent 20 by being placed on post 64, in accordance with some applications of the present invention. For some applications electrode 22 is a coiled electrode. Typically, the coiled electrode is disposed on an insulation tube 60, as shown in FIG. 3B. For example, the electrode may be coupled to the insulation tube, using adhesive, e.g., using ultraviolet (UV) (e.g., UV tape), or using adhesive, such as an epoxy adhesive. For some applications, stent 20 is shaped to define at least one post 64, as shown in FIG. 3A. The coiled electrode (typically coupled to the insulation tube) is coupled to the stent by being placed on the post. For some applications, the post is coupled to the stent at an intersection of two struts 65 of the stent, and the post protrudes radially outwardly from the stent with respect to the struts, in order to facilitate contact between the electrode and the subject's blood vessel, upon placement of the stent inside the blood vessel. For example, the post may be disposed at an angle of more than 5 degrees with respect to a plane defined by the struts at the intersection of which the post is coupled. Alternatively, the post does not protrude radially outwardly from the stent with respect to the struts. Typically, the electrode is fixedly coupled to the post by an electrode-fixation member, for example, by placing a cap 66 on the post, such as to hold the electrode on the post. For some applications, the cap is fixedly coupled to the post, e.g., using UV, or using adhesive, such as an epoxy adhesive. For some applications, posts that are electrical insulators protrude from a distal end of the stent body, and a coiled electrode is coupled to the posts, as described in further detail hereinbelow.

For some applications, one or more posts 64 are defined by first strut portion 32 of stent 20, the first strut portion being configured to be placed in the subject's aortic arch, for example, as shown in FIGS. 2A-C. Alternatively or additionally, one or more posts 64 are defined by second portion 34 of the stent, which is placed downstream of the aorta with respect to the first portion of the stent, for example, as shown in FIG. 2A. Coiled electrodes are coupled to posts 64, e.g., as described hereinabove. For some applications, the second strut portion of the stent is placed in the descending aorta, or in a portion of the aortic arch that is downstream of the aortic arch with respect to the first portion, and coiled electrodes are disposed on posts defined by the second strut portion.

Figure 4:
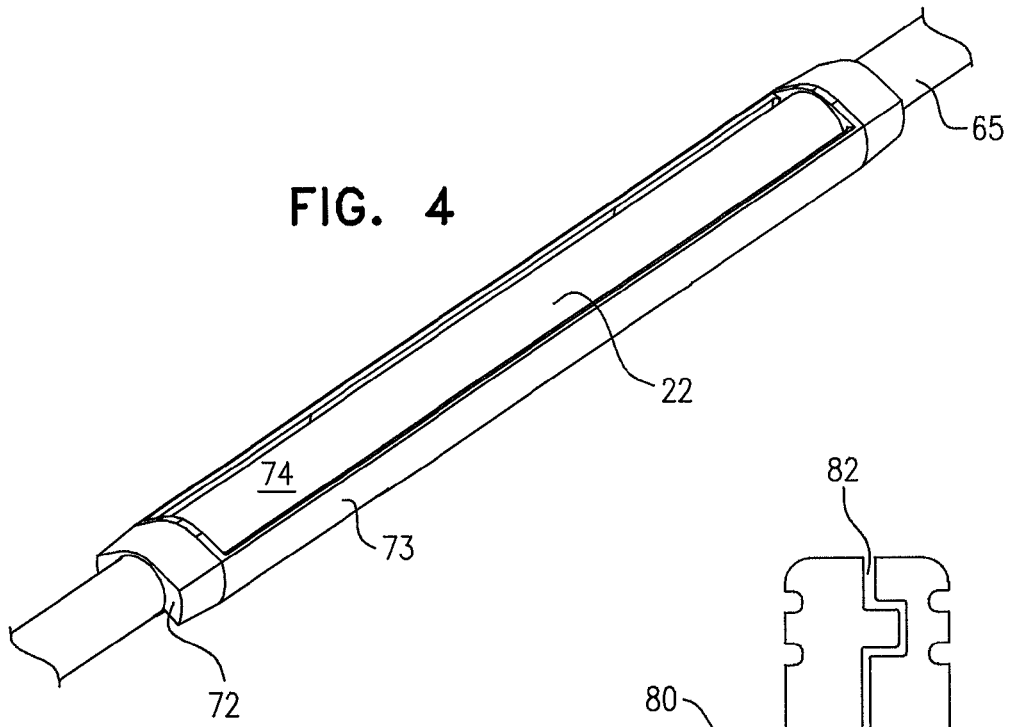
FIG. 4 is a schematic illustration of an electrode configured to be coupled to a stent, in accordance with some applications of the present invention.

Reference is now made to FIG. 4, which is a schematic illustration of electrode 22 coupled to a strut 65 of stent 20, in accordance with some applications of the present invention. For some applications, electrode 22 is mechanically coupled to strut 65 of stent 20. Alternatively or additionally, electrode 22 is coupled to post 64 (shown in FIG. 3A) of the stent. Typically, the electrode is disposed on an inner insulation tube 72. An outer insulation tube 73 is disposed over the electrode such as to insulate a first area of the electrode and such that a second area 74 of the electrode is exposed by the outer insulation tube. The second area of the electrode functions as the active area of the electrode.

Figure 5:
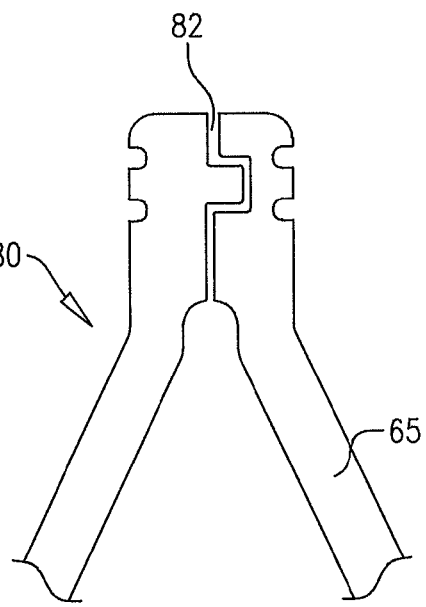
FIG. 5 is a schematic illustration of a mechanism for facilitating coupling of an electrode to a stent, in accordance with some applications of the present invention.

Reference is now made to FIG. 5, which is a schematic illustration of a mechanism 80 for facilitating coupling of electrode 22 to stent 20, in accordance with some applications of the present invention. For some applications, as shown, at an intersection 82 at which two struts 65 meet, the struts are separable from one another. A coiled electrode (e.g., as described hereinabove) is placed on one of the struts by separating the struts from one another and sliding the coiled electrode onto the strut. Subsequently, the struts are fixedly coupled to one another at the intersection, such as to fixedly couple the electrode to the strut. For example, the struts are coupled to one another by using laser welding, and/or sutures.

For some applications, stent 20 includes first, second, third, and fourth strut portions, and, correspondingly three junctions 37A, 37B, and 37C, e.g., as described herein with reference to FIGS. 2B-C, 6A-B, and 7E of the present application. For some applications, stent 20 includes first, second, and third strut portions, and, correspondingly two junctions 37A, and 37B, e.g., as shown in FIG. 2A and in FIGS. 7A-B of the present application. Alternatively, the stent may define first and second strut portions 32 and 34 that are coupled to each other at a single junction 37A, but may not include a third strut portion coupled to the second portion via springs (embodiment not shown).

For some applications, both first and second strut portions of the stent define posts, to which coiled electrodes 22 are couplable, e.g., as shown in FIG. 2A of the present application. Alternatively, only the first portion (i.e., the upstream-most, i.e., the distal-most portion) of the stent defines posts, to which coiled electrodes 22 are couplable, e.g., as shown in FIGS. 2B-C, 6A-B, 7A-B, and 7E of the present application.

Figure 6A:
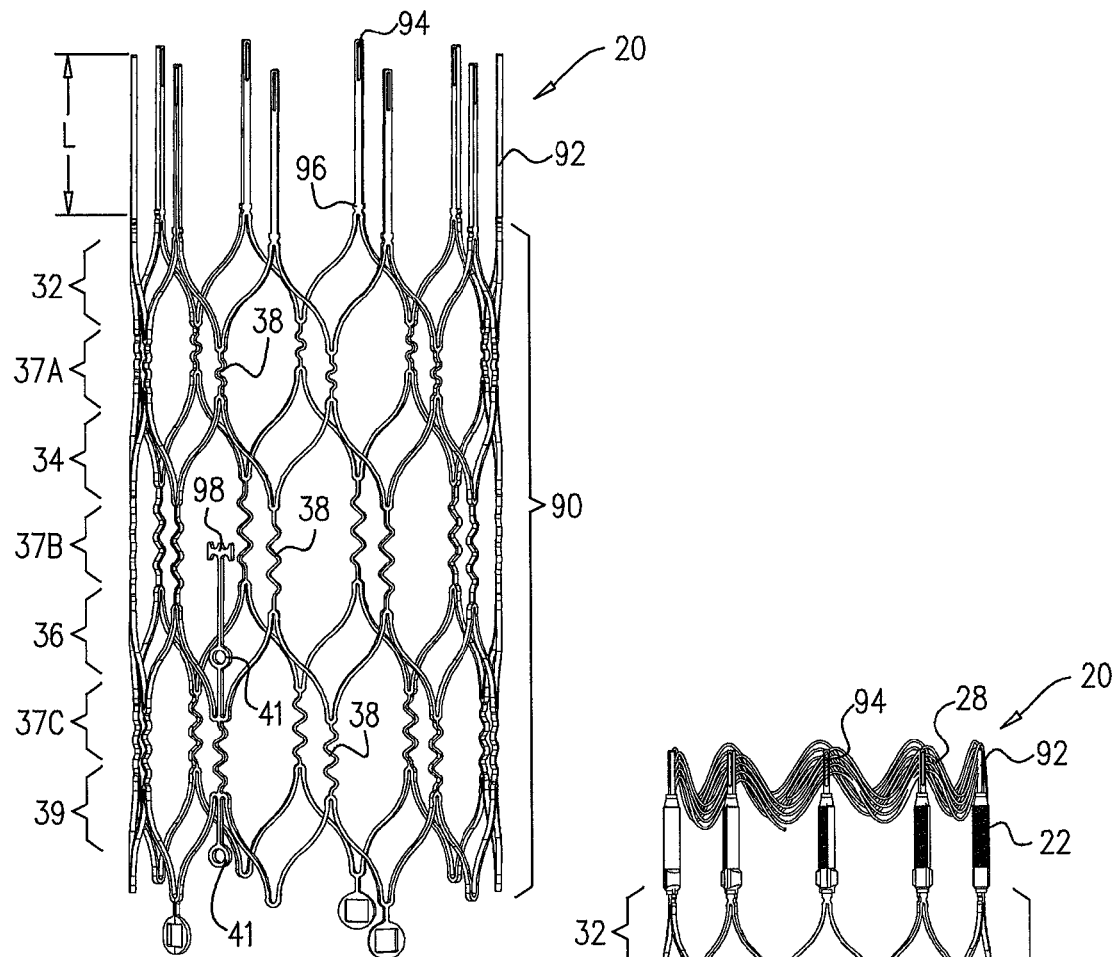
FIGS. 6A-B are schematic illustrations of a stent that defines a stent body with posts protruding from a distal end of the stent body, in accordance with some applications of the present invention.
Figure 6B:
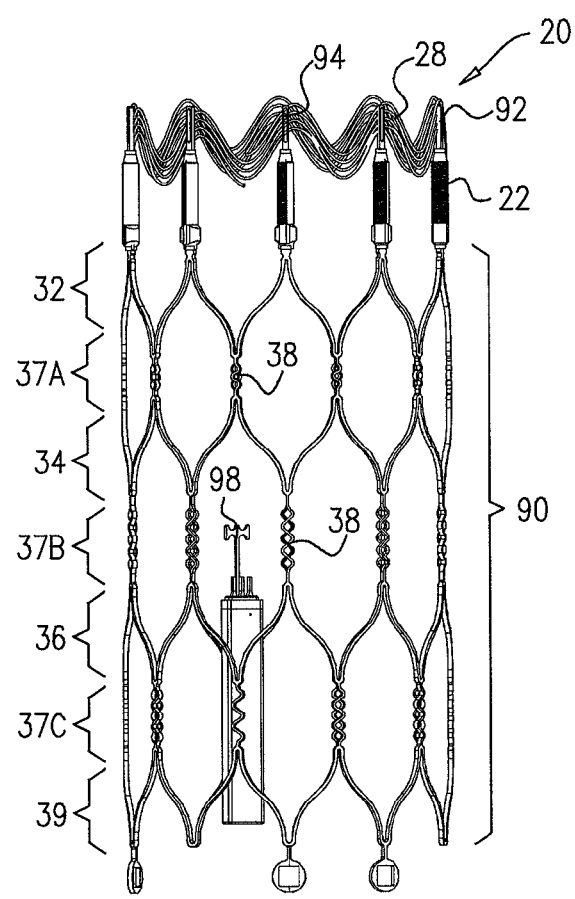

In accordance with respective applications, a single antenna 28 is coupled to the stent (as shown in FIGS. 2A-B, and FIG. 6B of the present application), or a plurality of antennas (e.g., two antennas) are coupled to the stent (embodiment not shown).

In general, the scope of the present invention includes stents having any number of strut portions coupled to each other at junctions (e.g., via springs), and any number of antennas, posts for supporting electrodes, and/or electrodes (e.g., coiled electrodes, as shown in FIG. 3B and FIG. 8A-B, or electrodes as shown in FIG. 4) coupled to the stent at any location on the stent, as would be obvious to one skilled in the art based upon the present disclosure, mutatis mutandis. The scope of the invention further includes stents having strut portions having sets of rings, such as sets of two to ten rings, e.g., two to six rings. In general, the term "strut portions" should be interpreted as meaning portions of the stent that provide resistance against longitudinal compression of the stent, that permit radial compression of the stent, that permit transverse flexibility of the stent, and that are less compliant than the junctions of the stent.

For some applications, one or more components are coupled to stent 20, by coupling the components to a cuff (e.g., by printing the components on the cuff, by adhering the components to the cuff using adhesive, and/or by suturing the components to the cuff) and coupling the cuff to the stent (e.g., by suturing the cuff to the stent, or adhering the cuff the stent using adhesive), e.g., as described in U.S. Provisional Patent Application 61/532,660 to Dagan, which is incorporated herein by reference. For example, antenna 28, electrodes 22, and/or capsule 30 may be coupled to the stent in the aforementioned manner. For some applications, a cuff is used that is configured to be coupled to the stent along substantially the entire length of the stent. Alternatively, a cuff such is used that is configured to be coupled to a portion of the length of the stent, e.g., first strut portion 32 of the stent.

Reference is now made to FIGS. 6A-B, which are schematic illustrations of stent 20, stent 20 defining a stent body 90 with posts 92 protruding longitudinally from a distal end of the stent body, in accordance with some applications of the present invention. FIG. 6A shows the stent and posts without the electrical components of the stent (such as electrodes 22, antenna 28 or capsule 30) disposed on the stent, and FIG. 6B shows the stent and posts with the aforementioned electrical components disposed thereon. As shown in FIG. 6B, antenna 28 is disposed annularly on distal portions of the posts, e.g., by being threaded through holes 94 defined by the distal portions of the posts. Thus, the posts longitudinally separate the antenna from the distal end of the stent body (e.g., from the distal-most closed loop of struts of the stent body).

For some applications, the posts at least partially electrically insulate the antenna from the stent body, due to electrical resistance provided by the posts or portions thereof. For some applications, posts 92, or at least portions thereof, are formed from a material that is an electrical insulator, such as a plastic. Typically, the posts are formed of nitinol, and the nitinol posts provide electrical resistance that is such that the current from the antenna to the stent body, through the posts, is relatively low, e.g., negligible, and/or substantially zero.

As described hereinabove, for some applications antenna 28 is used to receive electrical power for powering the control capsule 30 to drive a current via electrodes 22. Typically, the antenna receives power via inductive coupling, e.g., by transmitter 24 (shown in FIG. 1), or a different transmitter, transmitting RF energy toward antenna 28, such as to generate a magnetic field through the antenna. The magnetic field passing through antenna 28 generates an inductive current through antenna 28. The current through antenna 28 in turn generates a magnetic field, which can generate an inductive current through stent body 90, which may interfere with the antenna current, and reduce the efficiency of the electrical powering of the control capsule. For some applications, by separating the antenna from the distal end of the stent body, the posts reduce the strength of the inductive current that is generated in the stent body, thereby increasing the efficiency of the electrical powering of the control capsule, via the inductive current that is generated through the antenna.

For some applications, a length L (FIG. 6A) of each of posts 92 is less than 20 mm, e.g., less than 15 mm, and/or greater than 1 mm, e.g., greater than 5 mm Typically, coiled electrodes 22 are coupled to stent 20 by being placed around posts 92, for example, by using a construction as shown in FIGS. 8A-B. For some applications, the stent is shaped to define protrusions at the joints between the stent body and the posts. The protrusions act as stoppers 96 to support the electrode constructions, and to prevent the electrode constructions from sliding proximally with respect to the stent body.

Typically, antenna 28 is wiredly coupled to control capsule 30 (wires not shown), and the control capsule is powered using the inductive current of the antenna. For some applications, the inductive current of the antenna is the only source of power for the control capsule. The control capsule is typically configured to drive a current into the blood vessel via electrode 22 (e.g., to stimulate the blood vessel), and/or to receive an electrical parameter of the blood vessel via the electrode. For some applications, stent body 90 includes a wire holder 98 that is configured to hold in place with respect to the stent body the wires that couple the antenna to the control capsule, by the wires being threaded through slots defined by the wire holder.

Reference is now made to FIGS. 7A-B, which are schematic illustrations of stent 20, stent 20 defining a stent body 90 with posts 92 protruding from a distal end of the stent body, in accordance with some applications of the present invention.

Stent 20 as shown in FIG. 7A is generally similar to stent 20 as shown in FIG. 6A except for the following differences. Stent 20 as shown in FIG. 7A defines only two junctions 37A and 37B (and correspondingly three strut portions 32, 34, and 36), whereas stent 20 as shown in FIG. 6A defines three junctions 37A, 37B, and 37C (and correspondingly four strut portions 32, 34, 36, and 39). In addition, on the stent shown in FIG. 7A, coupling elements 41 for facilitating coupling of the control capsule to the stent are disposed on the distal half of the stent, whereas on the stent shown in FIG. 6A, coupling elements 41 for facilitating coupling of the control capsule to the stent are disposed on the proximal half of the stent. Furthermore, stent 20 as shown in FIG. 7A defines a pair of anchoring barbs 93 and 95, which protrude from struts of the stent and are, respectively, proximally-facing and distally-facing. In accordance with some applications of the present invention, a stent is used that defines a pair of anchoring barbs 93 and 95, which protrude from struts of the stent and are, respectively, proximally-facing and distally-facing, for example, as shown in FIG. 7A. The barbs typically facilitate anchoring of the stent to the blood vessel upon expansion of the stent within the blood vessel, by the barbs becoming embedded into the wall of the blood vessel.

Stent 20 as shown in FIG. 7B is generally similar to stent 20 as shown in FIG. 7A, except that barbs 93 and 95 of the stent shown in FIG. 7B are coupled to the stent at (or in the vicinity of) respective intersections between pairs of struts of the stent, whereas barbs 93 and 95 of the stent shown in FIG. 7A are coupled to the stent by protruding from the side of respective struts of the stent.

Reference is now made to FIGS. 7C-D, which are schematic illustration of respective views of barb 93 of stent 20, barb 93 being as shown in FIG. 7B. As can be seen from FIG. 7C, which shows a top view of the barb, the barb protrudes from the vicinity of an intersection of two struts 65 of the stent. As can be seen from FIG. 7D, which shows a side view of the barb, the stent is typically configured such that when the stent is open, the barb is raised from a plane that is defined by struts 65. Typically the barb is raised such that a height h of the tip of the barb from the plane defined by the struts is greater than 0.5 mm (e.g., greater than 0 8 mm), and/or less than 2 mm (e.g., less than 1.5 mm) Further typically, the barb curves away from the plane defined by the struts, a radius of curvature r of the barb being greater than 2 mm (e.g., greater than 4 mm), and/or less than 12 mm (e.g., less than 8 mm). Typically the height and curvature of the barb are such that when the stent is opened inside the blood vessel the barb becomes automatically embedded in the wall of the blood vessel without requiring distal or proximal movement of the stent with respect to the blood vessel in order to cause the barb to become embedded.

Figure 7E:
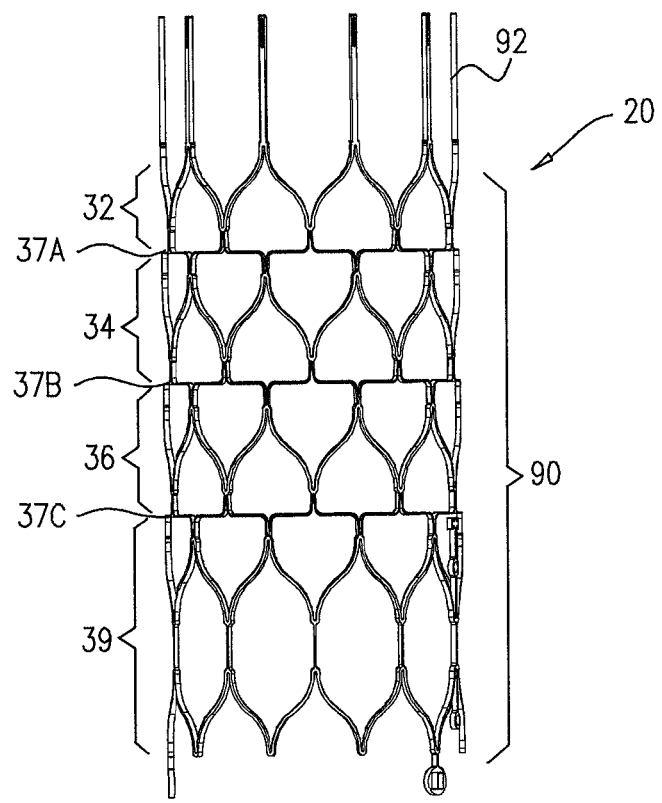
FIG. 7E is a schematic illustration of a stent that defines a stent body with posts protruding from a distal end of the stent body, in accordance with some additional applications of the present invention.
Figure 9A:
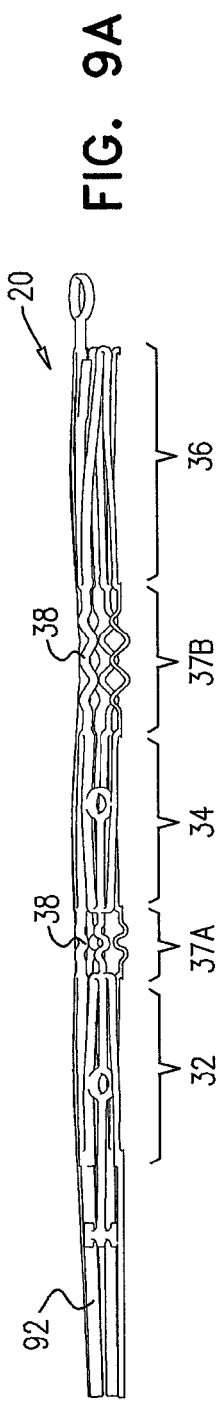
Figure 9B:
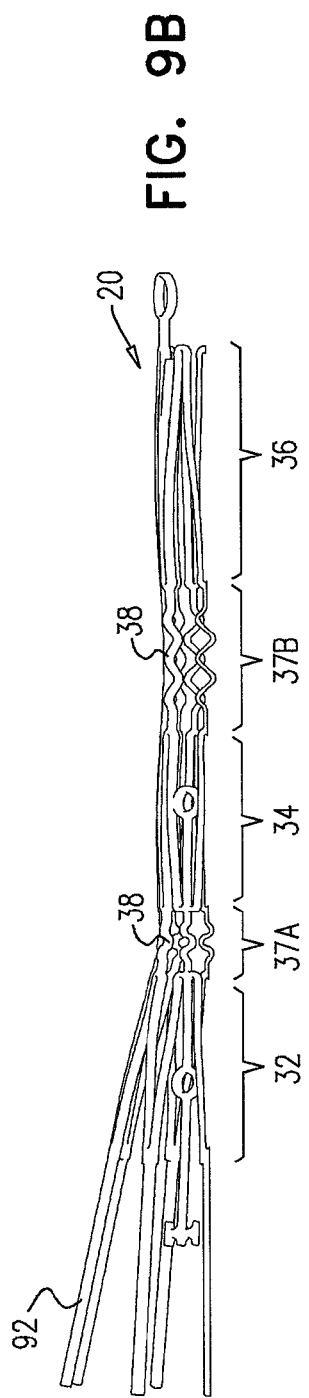
Figure 9C:
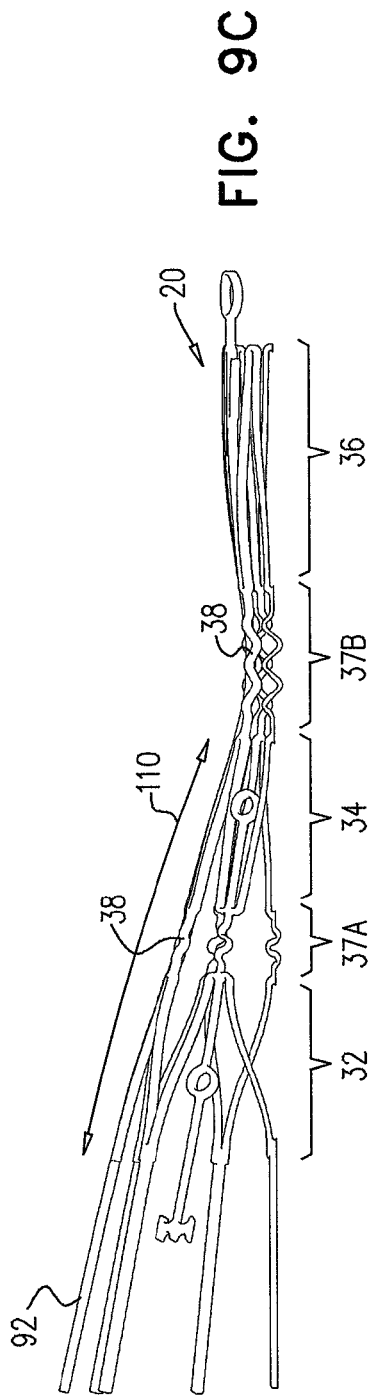
Figure 10A:
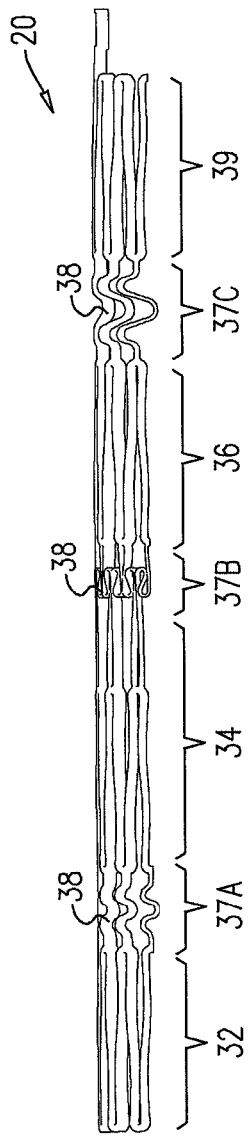
Figure 10B:
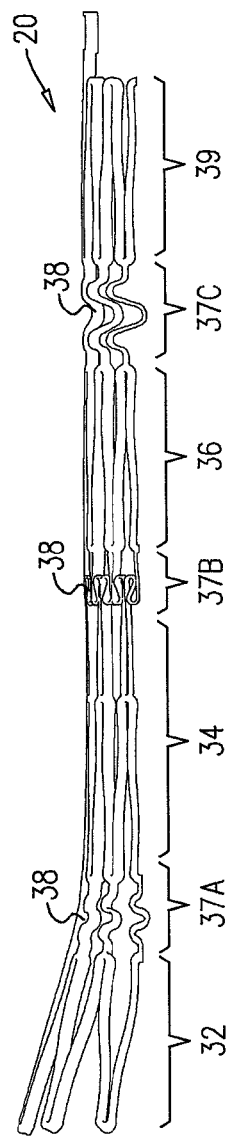
Figure 10C:
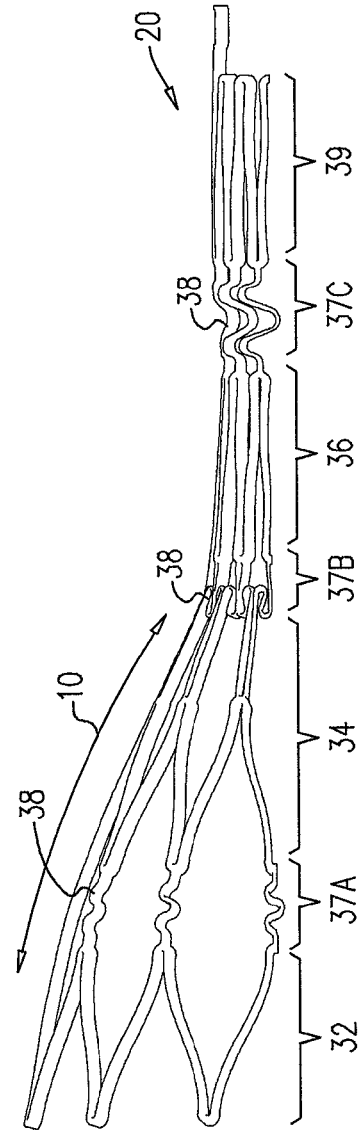

Reference is now made to FIG. 7E, which is a schematic illustration of stent 20, stent 20 defining a stent body 90 with posts 92 protruding from a distal end of the stent body, in accordance with some applications of the present invention. Stent 20 as shown in FIG. 7E is generally similar to stent 20 as shown in FIG. 6A except that the junctions of the stent that are shown in FIG. 7E are different from the junctions as shown in FIG. 6A. Junctions 37A-C of stent 20 as shown in FIG. 7E comprise longitudinal locations along the stent body at which the struts of the stent are shaped such as to facilitate bending of the stent at those locations.

Reference is now made to FIGS. 8A-B, which are schematic illustrations of an electrode construction 100 for coupling coiled electrodes 22 to posts 92 of stent 20, in accordance with some applications of the present invention. Typically, the electrode construction is configured such that electrode 22 is electrically isolated from the antenna and from the stent body.

For some applications, the coiled electrode is disposed around an insulting layer 102. For example, the insulating layer may be composed of polyether ether ketone (PEEK), and/or or another plastic. The insulating layer is typically hollow, such that the insulating layer can be placed on post 92 of stent 20. For some applications, the insulating layer is shaped to define an inner cross-section having a square shape. The square shaped cross-section of the inner surface is configured to prevent rotation of the electrode construction about post 92. The insulating layer acts in a generally similar manner to insulation tube 60 described hereinabove, with reference to FIG. 3B.

Typically, electrode construction 100 defines a tip-encapsulation portion 106 configured to hold the distal end of coiled electrode 22 in place with respect to insulating layer 102, by encapsulating the distal end of electrode 22. Further typically, electrode construction 100 defines a base-encapsulation portion 104 configured to hold the proximal end of coiled electrode 22 in place with respect to insulating layer 102, by encapsulating the proximal end of electrode 22. Typically, a proximal end 110 of the coiled electrode passes through the base-encapsulation portion. A wire from the control capsule is electrically coupled to the proximal end of the coiled electrode.

For some applications, the electrode construction defines an outer insulating layer 108. The outer insulating layer is placed around the side of the coiled electrode that faces the inside of the stent, in order to electrically insulate the electrode from the subject's blood.

Reference is now made to FIGS. 9A-E, which are schematic illustrations of respective steps of the opening of stent 20, the stent defining two junctions 37A and 37B, in accordance with some applications of the present invention. First and second strut portions 32 and 34 of the stent are flexibly coupled to one another at first junction 37A, and second and third strut portions 34 and 36 are flexibly coupled to one another at second junction 37B. By way of illustration, FIGS. 9A-E show the opening of a stent that is as shown in FIG. 7A, although the manner of the opening of any of the stents that define two or more junctions that are described herein would be generally similar.

As described hereinabove, stent 20 is typically configured to be placed inside the blood vessel (e.g., the aorta) percutaneously, e.g., using a 12 Fr-20 Fr catheter (e.g., a 16 Fr catheter). Typically, upon being placed inside the blood vessel, the stent is partially deployed, such that (a) electrodes 22 (not shown, but which are typically coupled to first, distal-most strut portion 32) contact the wall of the blood vessel at a given location within the blood vessel, and (b) a proximal portion of the stent is disposed inside the catheter, such that the stent may be retrieved into the catheter. The response of the subject to electrical stimulation of the blood vessel at the current location of the electrodes within the blood vessel is determined. In response thereto, the stent is (a) fully deployed at the current location of the stent (b) retrieved into the catheter and redeployed at a different location within the blood vessel, or (c) retrieved into the catheter and removed from the subject's body (e.g., if the subject does not respond in a suitable manner to electrical stimulation of the blood vessel at any locations at which the stent is deployed).

For some applications, junctions 37 of stent 20 are configured to cause at least a portion of the outer surface of the stent to assume a convex profile upon protruding from catheter. For example, as shown in the transition from FIG. 9B to FIG. 9C and from FIG. 9C to FIG. 9D, first junction 37A, causes at least a portion of the outer surface of stent 20 to assume a convex profile upon protruding from the catheter (as indicated by arrow 110). Typically, causing the outer surface of the stent to assume the convex profile, causes the angle that the outer surface of the stent makes with the vessel wall, as the stent protrudes from the catheter, to be less than if the stent were to assume a straight profile upon protruding from the catheter. For some applications, by reducing the angle that the outer surface of the stent makes with the vessel wall, damage to the vessel wall that could be caused by the distal end of the stent contacting the vessel wall is reduced. For some applications, the assumption of the convex profile by the outer surface of the stent brings the electrodes into contact with the vessel wall.

For some applications, junctions 37 of the stent are configured to facilitate retrieval of the stent into the catheter. For example, as shown in the transition from FIG. 9A to FIG. 9B, the flexible coupling between first strut portion 32 and second strut portion 34 that is provided by junction 37A allows first strut portion 32 to radially expand, while second strut portion 34 may remain substantially compressed inside the catheter. Similarly, as shown in the transition from FIG. 9D to FIG. 9E, the flexible coupling between second strut portion 34 and third strut portion 36 that is provided by junction 37B allows second strut portion 34 to radially expand, while third strut portion 36 may remain substantially compressed inside the catheter. In order to retrieve the stent into the catheter, the proximal end of the stent is pulled, such as to cause second portion 34 to become compressed by flexing about junction 37B. The proximal end of the stent then continues to be pulled, such as to cause first portion 32 to become compressed by flexing about junction 37A.

For some applications, first junction 37A of stent 20 is configured to reduce an angle that posts 92 of the stent make with the blood vessel wall as the posts protrude from the distal end of the delivery device, relative to the angle that the posts would make with the blood vessel wall in the absence of the junction. For some applications, in this manner, the first junction reduces injury to the blood vessel wall that may be caused by the posts, relative to if the posts were to make a larger angle with the blood vessel wall. For some applications, the first junction includes waved strips of nitinol (or another alloy or metal) that function as springs, each of the strips having a width that is greater than 0.1 mm, and/or less than 1 mm (e.g., less than 0.6 mm).

Reference is now made to FIGS. 10A-E, which are schematic illustration of respective steps of the opening of stent 20, stent 20 defining three junctions 37A, 37B, and 37C, in accordance with some applications of the present invention. First and second strut portions 32 and 34 of the stent are flexibly coupled to one another at first junction 37A, second and third strut portions 34 and 36 are flexibly coupled to one another at second junction 37B, and third and fourth strut portions 39 and 39 are flexibly coupled to one another at third junction 37C. By way of illustration, FIGS.

9A-E show the opening of a stent that is as shown in FIG. 2C, although the manner of the opening of any of the stents that define three or more junctions that are described herein would be generally similar.

As described hereinabove, with reference to FIGS. 9A-E, junctions 37 of stent 20 are configured to cause at least a portion of the outer surface of the stent to assume a convex profile upon protruding from catheter. For some applications, causing the outer surface of the stent to assume the convex profile reduces damage to the vessel wall that could be caused by the distal end of the stent contacting the vessel wall, relative to if the stent were to assume a straight profile upon protruding from the catheter. For some applications, the assumption of the convex profile by the outer surface of the stent brings the electrodes into contact with the vessel wall. For some applications, junctions 37 of the stent are configured to facilitate retrieval of the stent into the catheter, as described with reference to FIGS. 9A-E.

As described hereinabove, typically, the number of junctions that the stent defines increases as the length of the stent increases. For some applications, the length of the stent that is used increases as the diameter of the vessel in which the stent is to be placed increases, in order to facilitate greater radial expansion of the distal end of the stent during partial deployment of the stent. In addition, the length of the stent that is used increases as the curvature of the vessel in which the stent is to be placed increases, in order to facilitate greater radial expansion of the distal end of the stent during partial deployment of the stent. In a curved vessel, it may be necessary to radially expand the stent to a greater diameter than is necessary in a similar sized straight vessel, in order to bring the electrodes into contact with a portion of the vessel wall that is curving away from the distal end of the delivery system. Furthermore, in a curved vessel, the distal end of the delivery system via which the stent is inserted is typically disposed closer to the wall on one side of the vessel, and not disposed in the center of the vessel, due to the catheter tip typically being substantially straight, and the vessel being curved. Therefore, in a curved vessel, it may be necessary to radially expand the stent to a greater diameter than is necessary in a similar sized straight vessel, in order to bring the electrodes into contact with the wall that is further from the distal end of the delivery system.

Figure 11:
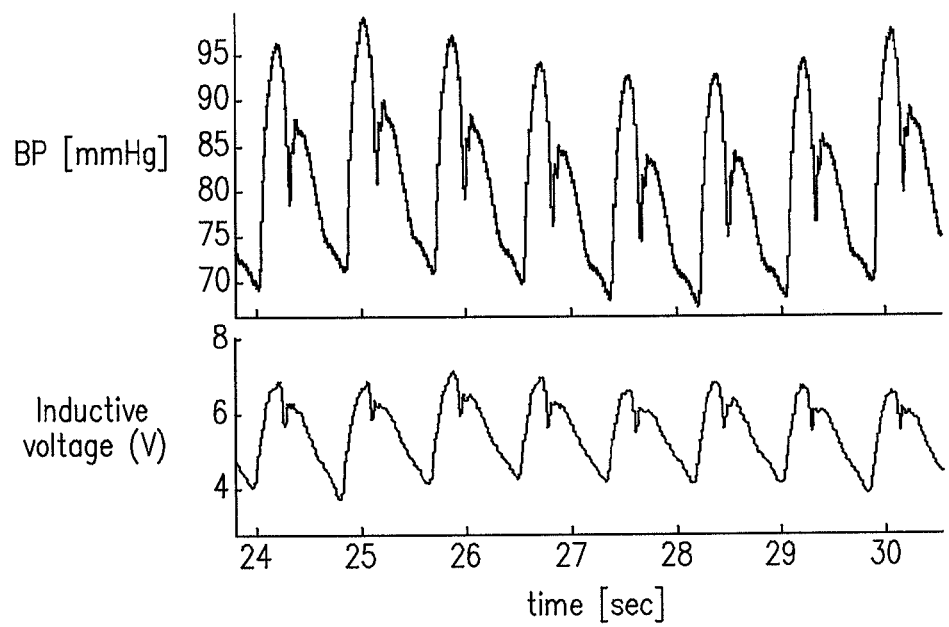
FIG. 11 is a graph showing experimental results that demonstrate a correlation between the variation with time of an inductive voltage that was measured in an antenna, and a component of the subject's blood pressure signal that relates the subject's cardiac cycle, in accordance with some applications of the present invention.
Figure 12:
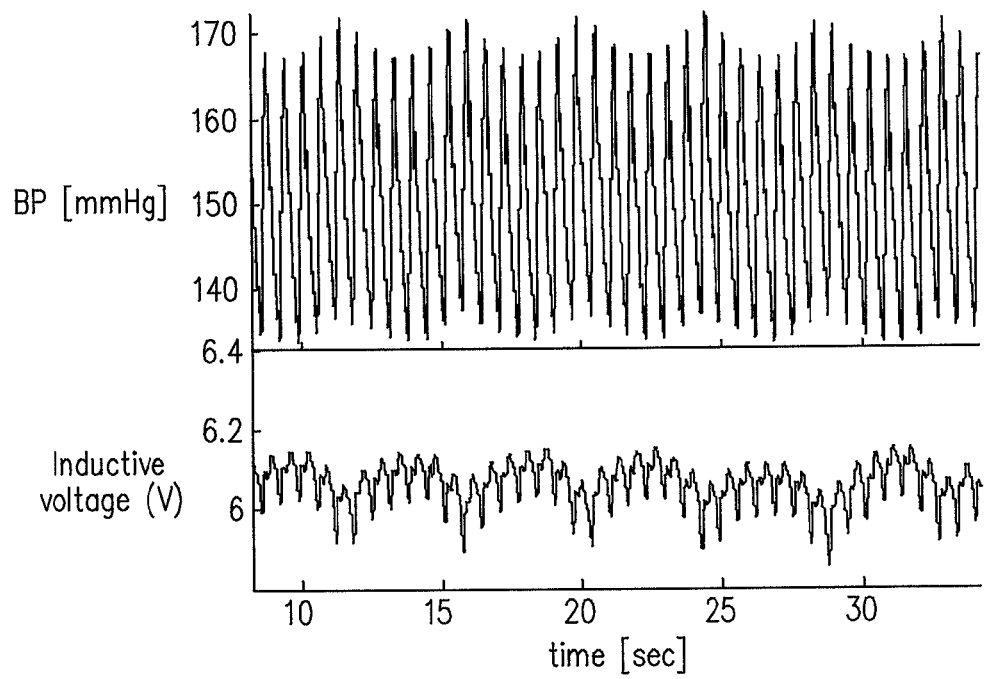
FIG. 12 is a graph showing experimental results that demonstrate a correlation between the variation with time of the inductive voltage that was measured in the antenna, and a component of the subject's blood pressure signal that relates the subject's respiratory cycle, in accordance with some applications of the present invention.

Reference is now made to FIGS. 11 and 12. FIG. 11 is a graph showing experimental results that demonstrate a relationship between the variation with time of an inductive voltage that was measured in an antenna, and a component of the subject's blood pressure signal that relates the subject's cardiac cycle, in accordance with some applications of the present invention. FIG. 12 is a graph showing experimental results that demonstrate a correlation between the variation with time of the inductive voltage that was measured in the antenna, and a component of the subject's blood pressure signal that relates the subject's respiratory cycle, in accordance with some applications of the present invention.

An antenna that was disposed on a stent was placed inside the aorta of a sheep. A transmitter that was disposed outside the sheep's body was used to transmit RF energy toward the antenna. Wires were used to connect the antenna to a computer that was disposed outside of the sheep's body, in order to record the inductive voltage that was generated at the antenna, as a result of the RF energy that was transmitted toward the antenna. Simultaneously with the detection of the inductive voltage at the antenna, the sheep's blood pressure was measured using a sphygmomanometer that was connected to a leg of the sheep.

The bottom curve of the graph of FIG. 11 shows the variation of the inductive voltage of the antenna with time, the x-axis of the graph measuring 1 second time periods. The top curve of the graph of FIG. 11 shows the simultaneously-measured blood pressure of the sheep. It may be observed that the inductive voltage signal is correlated to the blood pressure signal. The inventors of the present invention hypothesize that the variation of the inductive voltage of the antenna that correspond with the blood pressure signal is due to variations in the circumference of the antenna over the course of the subject's cardiac cycle. Since the antenna is disposed on a stent and the radial expansion of the stent is limited by the circumference of the blood vessel, the circumference of the antenna varies over the course of the subject's cardiac cycle, as the circumference of blood vessel varies, and in turn, the circumference of the stent varies.

The bottom curve of the graph of FIG. 12 shows the variation of the inductive voltage of the antenna with time, the x-axis of the graph measuring 5 second time periods. The top curve of the graph of FIG. 12 shows the simultaneously-measured blood pressure of the sheep. It may be observed that in both the inductive voltage signal and in the blood pressure signal there is an envelope having a period of approximately 5 seconds. For example, in the top graph of FIG. 12, the envelope peaks at around 20 seconds, and then peaks again at around 24.5 seconds. The envelope of the blood pressure signal is indicative of the subject's respiratory cycle. It may be observed that the envelope of inductive voltage signal is correlated to the envelope of the blood pressure signal. The inventors hypothesize that the variation of the inductive voltage of the antenna that correspond with the envelope blood pressure signal is due to the antenna moving with respect to the transmitter, as the subject's abdomen undergoes movement due to the subject's breathing. It is noted that, in FIG. 12, the troughs in the inductive voltage signal correspond to peaks in the blood pressure signal, whereas, in FIG. 11, the troughs in the inductive voltage signal correspond to troughs in the blood pressure signal. The inventors hypothesize that this is because the effect on the inductive voltage of the antenna moving with respect to the transmitter over the course of the subject's respiratory cycle, overrides the effect on the inductive voltage of the subject's blood pressure envelope varying over the course of the respiratory cycle.

Therefore, in accordance with some applications of the present invention, an annular antenna is placed inside a blood vessel on a stent, such that the radial expansion of the stent (and therefore the antenna) is limited by the circumference of the blood vessel. Alternatively, a stent, or at least a portion thereof, is configured to act as an antenna, the stent being placed inside a blood vessel such that the radial expansion of the stent is limited by the circumference of the blood vessel. An inductive current is generated in the antenna by transmitting RF energy toward the antenna. For some applications, RF energy is directed toward the antenna, the RF energy having a frequency of more than 50 kHz (e.g., more than 90 kHz), and/or less than 100 MHz (e.g., less than 60 MHz). The inductive current that is generated at the antenna is measured. Variations in the inductive current that are measured at the antenna are interpreted as being caused by variations in the geometry of the antenna over the course of the subject's cardiac cycle. For example, variations in the inductive current having a frequency of more than 0.5 Hz and/or less than 1.5 Hz are interpreted as being caused by variations in the geometry of the antenna over the course of the subject's cardiac cycle. For some applications, variations in the inductive current having a frequency of more than 0.05 Hz and/or less than 0.3 Hz are interpreted as being caused by variations in the geometry of the antenna over the course of the subject's respiratory cycle. In response to variations in the inductive current of the antenna, physiological parameters of the subject, e.g., hemodynamic physiological parameters of the subject, are derived. For example, the subject's cardiac rate, respiratory rate, blood pressure, blood vessel pulsation, and/or other parameters of the subject may be derived.

It is noted that, although some applications of the present invention have been described as being used in conjunction with a stent, the scope of the present invention includes applying the apparatus and methods described herein to a stent graft, mutatis mutandis. For example, a stent graft that defines strut portions and junctions may be used, and/or an antenna may be coupled to the body of a stent graft via posts that longitudinally separate the antenna from a distal end of the body of the stent graft, in accordance with the techniques described hereinabove.

Although some applications of the present invention have been described with respect to placing stent 20 inside a subject's aorta, the scope of the present invention includes placing stent 20 in other blood vessel's of a subject's body, mutatis mutandis.

For some applications, the techniques described herein are practiced in combination with techniques described in WO 07/013065 to Gross, which is incorporated herein by reference. For some applications, the techniques described herein are practiced in combination with the techniques described in WO 09/095918, entitled "Peristaltic pump for treatment of erectile dysfunction," to Gross, which claims priority from U.S. Patent Application 2009/0198097 to Gross, the PCT application and the U.S. application being incorporated herein by reference. For some applications, the techniques described herein are practiced in combination with the techniques described in U.S. Patent Application 2009/0198097 to Gross, which is incorporated herein by reference. For some applications, the techniques described herein are practiced in combination with the techniques described in U.S. 2012/0035679 to Dagan, U.S. 2011/0137370 to Gross, and/or in U.S. 2010/0305392 to Gross, all of which applications are incorporated herein by reference.

For some applications, the methods described herein are performed in combination with the techniques described in WO 09/095920 to Gross, which is incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a blood vessel of a subject, comprising:
   an annular antenna configured to be placed inside the blood vessel such that radial expansion of the antenna is limited by a circumference of the blood vessel;
   a transmitter configured to generate an inductive current in the antenna, by transmitting RF energy toward the antenna;
   a control capsule comprising circuitry configured to measure the inductive current in the antenna, and, in response thereto, to determine blood pressure of the subject; and
   a tubular endovascular aortic stent having an outer diameter of 10-35 mm, wherein the antenna is coupled to the tubular endovascular aortic stent and the tubular endovascular aortic stent is configured to be disposed within the subject's body at an aortic site that is between the bifurcation of the aorta with the left subclavian artery and the bifurcation of the aorta with the fifth intercostal artery.

2. The apparatus according to claim 1, wherein the control capsule is configured to determine the blood pressure of the subject by interpreting variations in the inductive current that are measured at the antenna as being caused by variations in geometry of the antenna over the course of the subject's cardiac cycle.

3. The apparatus according to claim 1, wherein the transmitter is configured to transmit the RF energy at a frequency of 50 kHz-100 MHz.

4. The apparatus according to claim 3, wherein the transmitter is configured to transmit the RF energy at a frequency of 90 kHz-60 MHz.

5. The apparatus according to claim 3, wherein the transmitter is configured to transmit the RF energy at a frequency of more than 60 MHz.

6. The apparatus according to claim 1, wherein a length of the stent is 30-100 mm.

7. The apparatus according to claim 1, wherein the stent has a crimped profile of 10-18 Fr.

8. The apparatus according to claim 1, wherein the stent has a crimped profile of 8-18 Fr.

9. A method comprising:
   generating an inductive current, in an annular antenna that has been placed in an aorta of a subject and allowed to expand radially, such that radial expansion of the antenna is limited by a circumference of the aorta, by transmitting RF energy toward the antenna;
   measuring the inductive current in the antenna; and
   in response thereto, determining blood pressure of the subject,
   the method being performed using an apparatus comprising:
   the annular antenna;
   a transmitter which will generate the inductive current in the antenna, by transmitting the RF energy toward the antenna;
   a control capsule comprising circuitry which will measure the inductive current in the antenna, and, in response thereto, to determine the blood pressure of the subject; and
   a tubular endovascular aortic stent having an outer diameter of 10-35 mm, wherein the antenna is coupled to the tubular endovascular aortic stent and the tubular endovascular aortic stent is disposed within the subject's body at an aortic site that is between the bifurcation of the aorta with the left subclavian artery and the bifurcation of the aorta with the fifth intercostal artery.

10. The method according to claim 9, wherein determining the blood pressure comprises interpreting variations in the inductive current that are measured at the antenna as being caused by variations in geometry of the antenna over the course of the subject's cardiac cycle.

11. The method according to claim 9, wherein transmitting the RF energy comprises transmitting the RF energy at a frequency of 50 kHz-100 MHz.

12. The method according to claim 11, wherein transmitting the RF energy comprises transmitting the RF energy at a frequency of 90 kHz-60 MHz.

13. The method according to claim 11, wherein transmitting the RF energy comprises transmitting the RF energy at a frequency of less than 60 MHz.

14. The method according to claim 9, wherein a length of the stent is 30-100 mm.

15. The method according to claim 9, wherein the stent has a crimped profile of 10-18 Fr.

16. The method according to claim 9, wherein the stent has a crimped profile of 8-18 Fr.

* * * * *